(12) United States Patent
Suddaby

(10) Patent No.: US 11,172,969 B2
(45) Date of Patent: Nov. 16, 2021

(54) FUSION DEVICE

(71) Applicant: Loubert S. Suddaby, Orchard Park, NY (US)

(72) Inventor: Loubert S. Suddaby, Orchard Park, NY (US)

( * ) Notice: Subject to any disclaimer, the term of this patent is extended or adjusted under 35 U.S.C. 154(b) by 131 days.

(21) Appl. No.: 16/774,079

(22) Filed: Jan. 28, 2020

(65) Prior Publication Data
US 2021/0228250 A1   Jul. 29, 2021

(51) Int. Cl.
*A61B 17/86* (2006.01)
*A61B 17/16* (2006.01)
*A61F 2/30* (2006.01)

(52) U.S. Cl.
CPC ...... *A61B 17/8635* (2013.01); *A61B 17/1615* (2013.01); *A61B 17/863* (2013.01); *A61B 17/8665* (2013.01); *A61F 2/30988* (2013.01); *A61F 2002/3093* (2013.01); *A61F 2002/30579* (2013.01); *A61F 2002/30622* (2013.01); *A61F 2002/30995* (2013.01)

(58) Field of Classification Search
CPC ... A61B 17/86; A61B 17/8625; A61B 17/863; A61B 17/8635; A61B 17/864; A61B 17/8645; A61B 17/8665; A61B 2017/8655
See application file for complete search history.

(56) References Cited

U.S. PATENT DOCUMENTS

| | | | |
|---|---|---|---|
| 4,175,555 A | 11/1979 | Herbert | |
| 5,098,435 A * | 3/1992 | Stednitz | A61B 17/1637 411/387.5 |
| 5,478,342 A * | 12/1995 | Kohrs | A61B 17/8685 606/310 |
| 5,759,184 A * | 6/1998 | Santangelo | A61B 17/742 606/68 |
| 5,849,004 A * | 12/1998 | Bramlet | A61B 17/0401 606/232 |
| 6,030,162 A | 2/2000 | Huebner | |
| 6,183,474 B1 * | 2/2001 | Bramlet | A61F 2/4241 606/66 |

(Continued)

FOREIGN PATENT DOCUMENTS

| | | |
|---|---|---|
| CA | 2390912 | 1/2008 |
| EP | 3123970 | 2/2017 |
| FR | 2971138 | 8/2012 |

OTHER PUBLICATIONS

Rialto SI Fusion System Brochure, "A Unique Approach to Sacroiliac Joint Fusion Procedures", Medtronic, 2016.

(Continued)

*Primary Examiner* — Eric S Gibson
(74) *Attorney, Agent, or Firm* — Simpson & Simpson, PLLC; Michael Nicholas Vranjes

(57) ABSTRACT

A fusion device assembly for fusion of a joint, including a fusion device, including a distal end, a proximal end, a radially outward facing surface including threading, a bore extending from the proximal end, at least one flute arranged proximate the distal end, and at least one aperture arranged adjacent to the at least one flute, and a reversibly connected hollow drive shaft for insertion of said device which, in a some embodiments, is hollow to allow addition of supplementary bone graft materials or products, should this be desired, without altering the position of the deployed device.

20 Claims, 16 Drawing Sheets

(56) References Cited

U.S. PATENT DOCUMENTS

| | | | | |
|---|---|---|---|---|
| 7,708,738 B2* | 5/2010 | Fourcault | ............ | A61B 17/8635 |
| | | | | 606/67 |
| 7,780,710 B2* | 8/2010 | Orbay | ................ | A61B 17/8061 |
| | | | | 606/286 |
| 8,475,505 B2 | 7/2013 | Nebosky et al. | | |
| 8,579,947 B2 | 11/2013 | Wu | | |
| 8,617,226 B2* | 12/2013 | Kim | ..................... | A61B 17/864 |
| | | | | 606/310 |
| 8,945,193 B2* | 2/2015 | Kirschman | ........ | A61B 17/8841 |
| | | | | 606/304 |
| 8,992,587 B2* | 3/2015 | Kirschman | .......... | A61B 17/863 |
| | | | | 606/305 |
| 9,295,488 B2 | 3/2016 | Asfora | | |
| 9,308,035 B2* | 4/2016 | Biedermann | ...... | A61B 17/7258 |
| 9,358,056 B2 | 6/2016 | Stalcup et al. | | |
| 9,358,057 B1 | 6/2016 | Whipple et al. | | |
| 9,480,520 B2 | 11/2016 | Rampersaud et al. | | |
| 9,526,547 B2* | 12/2016 | Reed | ..................... | A61B 17/864 |
| 9,668,781 B2 | 6/2017 | Stark | | |
| 9,833,321 B2 | 12/2017 | Rindal et al. | | |
| 9,931,141 B2 | 4/2018 | Jimenez | | |
| 10,172,656 B1* | 1/2019 | Reimels | ............. | A61B 17/8605 |
| 10,251,688 B2 | 4/2019 | Asfora | | |
| 10,499,969 B2* | 12/2019 | McGirt | ............. | A61B 17/7032 |
| 10,864,029 B2* | 12/2020 | Redmond | .......... | A61B 17/8685 |
| 2002/0049447 A1* | 4/2002 | Li | .......................... | A61B 17/68 |
| | | | | 606/916 |
| 2002/0143401 A1* | 10/2002 | Michelson | ............ | A61F 2/4611 |
| | | | | 623/17.16 |
| 2002/0169453 A1* | 11/2002 | Berger | .................... | A61B 17/60 |
| | | | | 606/295 |
| 2003/0014054 A1 | 1/2003 | Huebner | | |
| 2003/0078584 A1 | 4/2003 | Tipirneni | | |
| 2003/0158557 A1* | 8/2003 | Cragg | .................... | A61F 2/4601 |
| | | | | 606/86 R |
| 2005/0177158 A1* | 8/2005 | Doubler | ............. | A61B 17/7225 |
| | | | | 606/64 |
| 2007/0233123 A1* | 10/2007 | Ahmad | ............... | A61B 17/863 |
| | | | | 606/307 |
| 2008/0009861 A1* | 1/2008 | Stark | ..................... | A61F 2/4601 |
| | | | | 606/914 |
| 2010/0057141 A1* | 3/2010 | Abdelgany | ........ | A61B 17/8685 |
| | | | | 606/310 |
| 2011/0213426 A1* | 9/2011 | Yedlicka | ............ | A61B 17/8635 |
| | | | | 606/309 |
| 2013/0018427 A1 | 1/2013 | Pham et al. | | |
| 2013/0123857 A1* | 5/2013 | Biedermann | ........ | A61B 17/744 |
| | | | | 606/303 |
| 2013/0310883 A1* | 11/2013 | Levy | ..................... | A61B 17/863 |
| | | | | 606/313 |
| 2013/0317503 A1 | 11/2013 | Songer et al. | | |
| 2014/0058460 A1* | 2/2014 | Reed | .................. | A61B 17/8635 |
| | | | | 606/312 |
| 2014/0094859 A1* | 4/2014 | Reed | ..................... | A61B 17/863 |
| | | | | 606/312 |
| 2014/0243912 A1* | 8/2014 | Mobasser | ............ | A61B 17/863 |
| | | | | 606/311 |
| 2014/0257412 A1 | 9/2014 | Patty et al. | | |
| 2015/0201979 A1* | 7/2015 | Paul | ..................... | A61B 17/7225 |
| | | | | 606/62 |
| 2016/0242820 A1* | 8/2016 | Whipple | ............ | A61B 17/8695 |
| 2016/0287301 A1* | 10/2016 | Mehl | ..................... | A61B 17/863 |
| 2017/0196608 A1 | 7/2017 | Castaneda et al. | | |
| 2017/0296245 A1* | 10/2017 | Gault | ..................... | A61B 17/864 |
| 2017/0296344 A1 | 10/2017 | Souza et al. | | |
| 2018/0055551 A1 | 3/2018 | Yalizis | | |
| 2018/0116814 A1 | 5/2018 | Sullivan et al. | | |
| 2018/0153698 A1 | 6/2018 | Rindal et al. | | |
| 2018/0235670 A1 | 8/2018 | Jimenez | | |
| 2019/0125371 A1* | 5/2019 | Asfora | ................. | A61B 17/864 |
| 2019/0125408 A1* | 5/2019 | Asfora | ............... | A61B 17/8625 |
| 2019/0231405 A1* | 8/2019 | Redmond | .......... | A61B 17/8685 |
| 2019/0231406 A1 | 8/2019 | Asfora | | |
| 2019/0388131 A1* | 12/2019 | Mehl | ..................... | A61B 17/864 |
| 2020/0038070 A1* | 2/2020 | Suddaby | ............... | A61F 2/4405 |
| 2020/0046413 A1* | 2/2020 | Thornes | ............... | A61B 17/863 |

OTHER PUBLICATIONS

Sicure® Sacroiliac Joint Fusion System Brochure, Alevio, LLC, Birmingham, AL, 2019.

www.spinemarketgroup@gmail.com, last accessed Apr. 15, 2020.

Acutrak 2® Headless Compression Screw System, Surgical Technique Guide Brochure, 2012 Acumed®, Hillsboro, OR, www.acumed.net, last accessed Apr. 15, 2020.

* cited by examiner

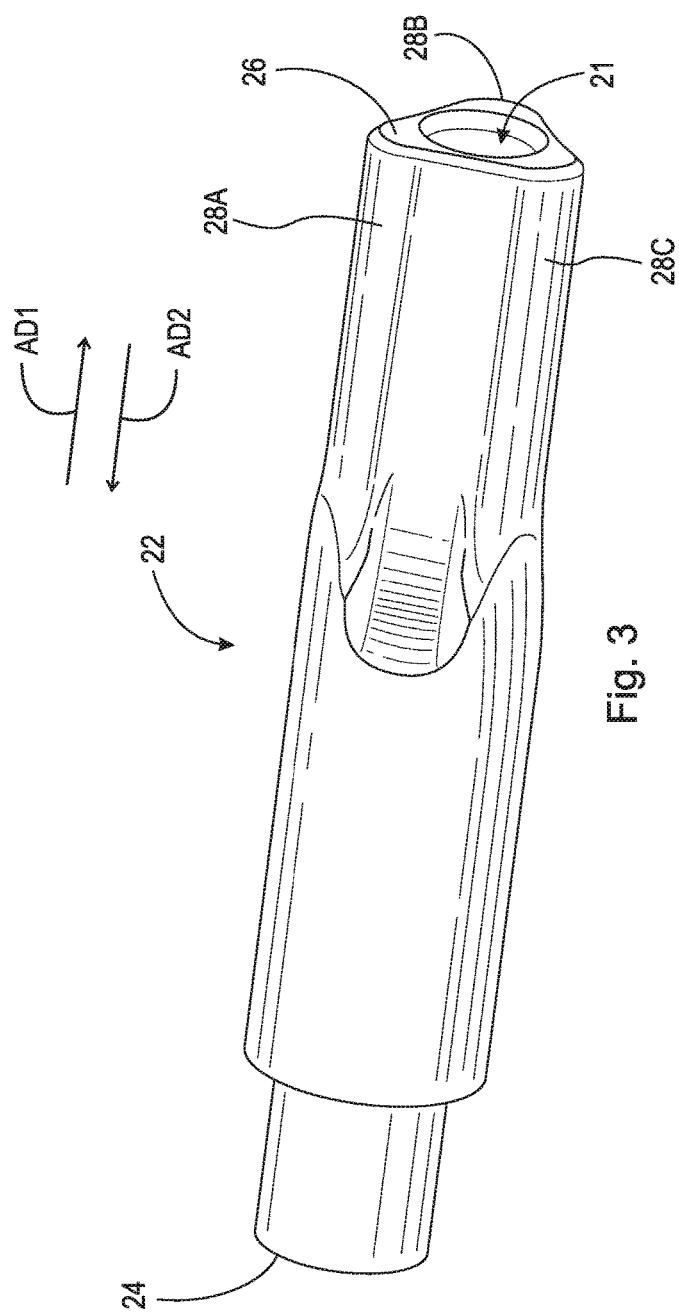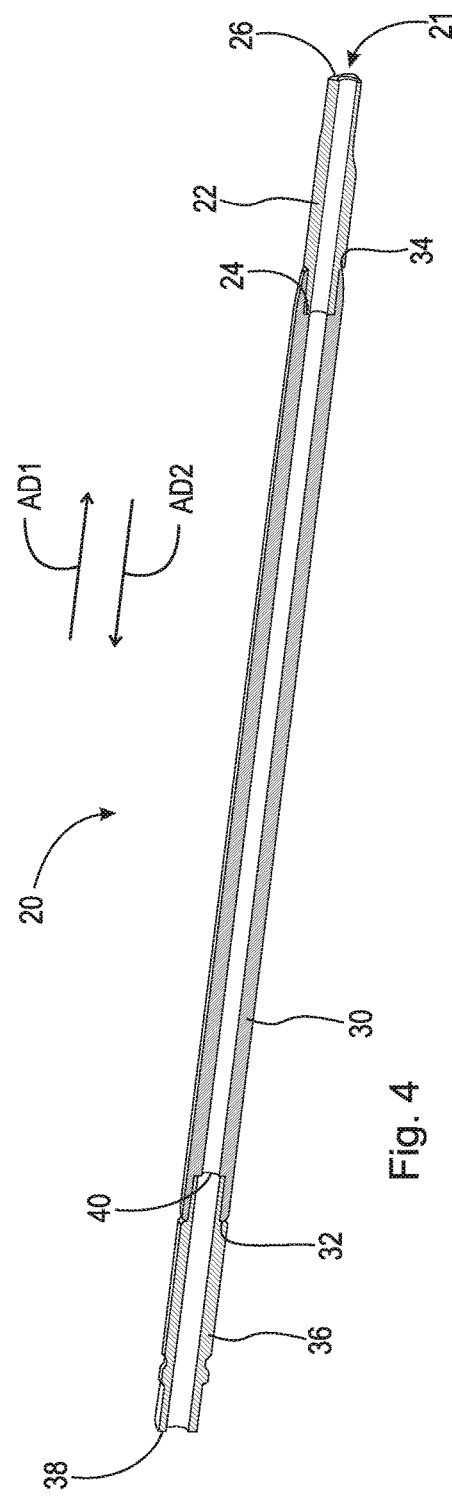

FUSION DEVICE

FIELD

The present disclosure relates to orthopedic surgery, and more particularly to interbone fixation fusion devices and especially interarticular joint fixation, specifically deep tissue joints such as spinal facet joints and sacroiliac (SI) joints.

BACKGROUND

Fusion of spinal elements has been a long-standing solution to symptoms of degenerating spinal discs. In fact, even though artificial discs have made some progress in the surgical arena, spinal fusion remains the most reliable means of alleviating symptoms referable to degenerating discs and is still the de facto gold standard.

One of the consequences of spinal fusion is adjacent level degeneration. Even though a normal functional spinal segment is fused, spinal motion must still occur, with forces being transferred to adjacent normal segments placing them under increases stress and contributing to a more rapid degenerative decline.

Since most spinal fusions are done in the low back and include the sacrum, which fuses naturally after birth, caudally transferred forces are dispersed to the sacroiliac (SI) joints causing abnormal stresses upon these joints.

While cranially transmitted forces simply go to the disc above, which can be fused by traditional means of interbody and/or posterolateral fusion, the SI joint is unique, complex, and difficult to visualize with traditional fluoroscopic methods.

Successful spinal fusions are often plagued after months or years of successful relief of symptomatology by a return of symptoms due to adjacent level degeneration. As many as twenty-five percent (25%) of cases of recurrent pain post spinal fusion are felt to be secondary to increased and abnormal motion at the level of the SI joint which can be severe.

While SI joint fusion procedures have been around for many years, recent trends have focused on minimally invasive ways to stabilize the joint thereby alleviating pain caused by the abnormal stresses placed upon them through natural degeneration or accelerated degeneration caused by spinal fusion. The addition of computerized guidance systems to the operating room armamentarium has afforded additional ways that stabilization of complex and deep-seated joints can be achieved surgically.

Thus, there is a long-felt need for a fusion device that allows fusion of deep-seated joints by way of minimally invasive surgery.

SUMMARY

According to aspects illustrated herein, there is provided a fusion device assembly for fusion of a joint, comprising a fusion device, including a distal end, a proximal end, a radially outward facing surface including threading, a bore extending from the proximal end, at least one flute arranged proximate the distal end, and at least one aperture arranged adjacent to the at least one flute.

According to aspects illustrated herein, there is provided a fusion device for fusion of a joint, comprising a distal end, a proximal end, a radially outward facing surface including threading, a bore extending from the proximal end, at least one flute arranged proximate the distal end, at least one aperture arranged adjacent to the at least one flute, at least one opening, and at least one expandable member operatively arranged in the bore to expand radially through the at least one opening.

According to aspects illustrated herein, there is provided a fusion device assembly for fusion of a joint, comprising a fusion device, including a distal end having a drill bit, a proximal end, a radially outward facing surface including threading, a bore extending from the proximal end, at least one flute arranged proximate the distal end, at least one aperture arranged adjacent to the at least one flute, at least one opening, and at least one expandable member operatively arranged in the bore to expand radially through the at least one opening, and a shaft, including a first end, a second end operatively arranged to be non-rotatably connected to the proximal end, and a through-bore extending from the first end to the second end.

According to aspects illustrated herein, there is provided a device for fixating the position of proximate elements of a dysfunctional sacroiliac (SI) joint, though it is recognized that miniaturization of the device would allow its use in smaller joints such as those in the lumbar facets, hands, and foot and ankle.

The device broadly comprises a cylindrical inter body implant including a self-drilling tip having full or partial threading internally and/or externally, and a hollow internal chamber into which bone drilling material from the advancing tip is funneled via flutes directing the material into apertures that perforate the device wall.

In a fully threaded iteration, the screw pitch is varied such that compression occurs gradually across the joint as the screw advances. In a partially threaded version, threads and flutes are found at the distal end, followed by a non-threaded perforated middle segment and then smaller pitched threads at the proximal end to facilitate joint compression in the manner of a lag-screw. In some embodiments, the device includes a fully threaded regular pitch bone screw configuration.

At the distal point or tip of the device, multiple configurations may be employed. In some embodiments, the tip is hollowed such that the device can be advanced along a guide wire, like a Kirschner wire (or K-wire). In some embodiments, the tip is a sharp point that is simply pressed into the bone surface such that it retains its position upon rotation in a manner approximating a Brad point drill bit tip. In some embodiments, the device is employed with image guidance where a previously placed guide wire is not necessary since real time information as to drill depth and direction is constantly available. The guide wire iteration is likely to be used in cases using traditional fluoroscopy, whereas the point tip version is expected to be used where image guided technology is available.

Once the tip is apposed to the bone surface, rotation of the device by hand or motor advances the tip of the device in a fashion similar to a standard self-drilling bone drill. Flutes at the tip direct bone drillings into the hollow chamber of the device, where they are housed as graft rather than directed back to the proximal drill hole as a normal twist drill would do. The flutes with their capture apparatus are located in the distal third, closer to the distal tip such that as much bone as possible that is harvested by the distal tip is directed into the inner graft chamber. More proximally, apertures exist in the shaft wall to allow the internal graft to communicate with the outer bone such that through-and-through fusion may occur. Such apertures may be round, oblong, spiral, rectangular, etc., and exist between threads or render the threads discontinuous as desired.

In some embodiments, the proximal end of the device is connected to a hollow drive shaft in a reversible fashion. The connection between the device and the hollow drive shaft may comprise any suitable connection known in the art. For example, a reverse thread screw connection, a press fit, a clasp or O-ring, or as a socket connection. In some embodiments, an image array may be connected to the hollow drive shaft so that the deployment of the device is fully image guided.

The hollow drive shaft, in turn, at its proximal end, is configured so as to permit engagement with hand or motor-powered attachments available in any standard orthopedic operating room. The shaft allows deployment of the device to its intended inter-bone target whereupon the hand or power drive attachment is removed leaving the device in situ with the hollow drive shaft emanating from the wound.

Additional bone product may be placed in the hollow drive shaft and a plunger or ramrod may be used to compress and compact the added bone graft into the device since evidence demonstrates that compression of bone elements facilitates fusion.

Once the graft is fully packed into the device, the plunger is held in place until the hollow shaft is disengaged and both the plunger and the shaft can be removed.

This process permits a safe and minimally invasive placement of a bone/fusion device. Rapid and accurate device placement lowers risks of infection and tissue trauma while reducing expensive operating room time.

By having the deployable device function as its own drill bit, drill tap, autograft harvester, joint fixator, and joint compressor, a SI joint fusion can be accomplished in a fraction of the time and with greater accuracy and success than heretofore possible.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which:

FIG. 3 is a front perspective view of a section of the shaft shown in FIG. 1;

FIG. 4 is a cross-sectional view of the shaft taken generally along line 4-4 in FIG. 2;

FIG. 6 is a cross-sectional view of the fusion device taken generally along line 6-6 in

FIG. 5A;

DETAILED DESCRIPTION

Figure 1:
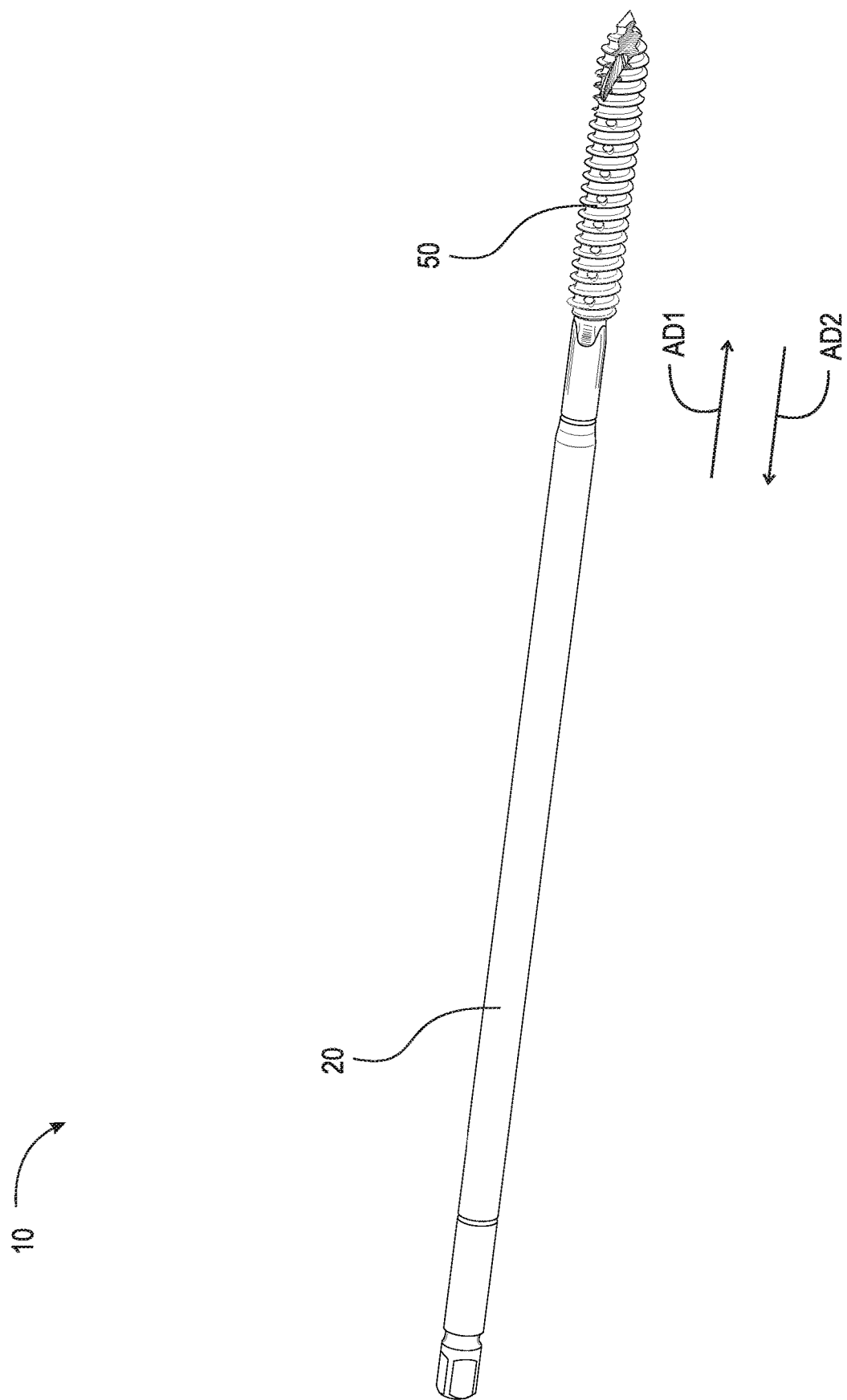
FIG. 1 is a front perspective view of a fusion device assembly.

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments. The assembly of the present disclosure could be driven by hydraulics, electronics, pneumatics, and/or springs.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

It should be understood that use of "or" in the present application is with respect to a "non-exclusive" arrangement, unless stated otherwise. For example, when saying that "item x is A or B," it is understood that this can mean one of the following: (1) item x is only one or the other of A and B; (2) item x is both A and B. Alternately stated, the word "or" is not used to define an "exclusive or" arrangement. For example, an "exclusive or" arrangement for the statement "item x is A or B" would require that x can be only one of A and B. Furthermore, as used herein, "and/or" is intended to mean a grammatical conjunction used to indicate that one or more of the elements or conditions recited may be included or occur. For example, a device comprising a first element, a second element and/or a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element.

Moreover, as used herein, the phrases "comprises at least one of" and "comprising at least one of" in combination with a system or element is intended to mean that the system or element includes one or more of the elements listed after the phrase. For example, a device comprising at least one of: a first element; a second element; and, a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element. A similar interpretation is intended when the phrase "used in at least one of:" is used herein. Furthermore, as used herein, "and/or" is intended to mean a grammatical conjunction used to indicate that one or more of the elements or conditions recited may be included or occur. For example, a device comprising a first element, a second element and/or a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element.

By "non-rotatably connected" elements, we mean that: the elements are connected so that whenever one of the elements rotate, all the elements rotate; and relative rotation between the elements is not possible. Radial and/or axial movement of non-rotatably connected elements with respect to each other is possible, but not required.

Figure 2:
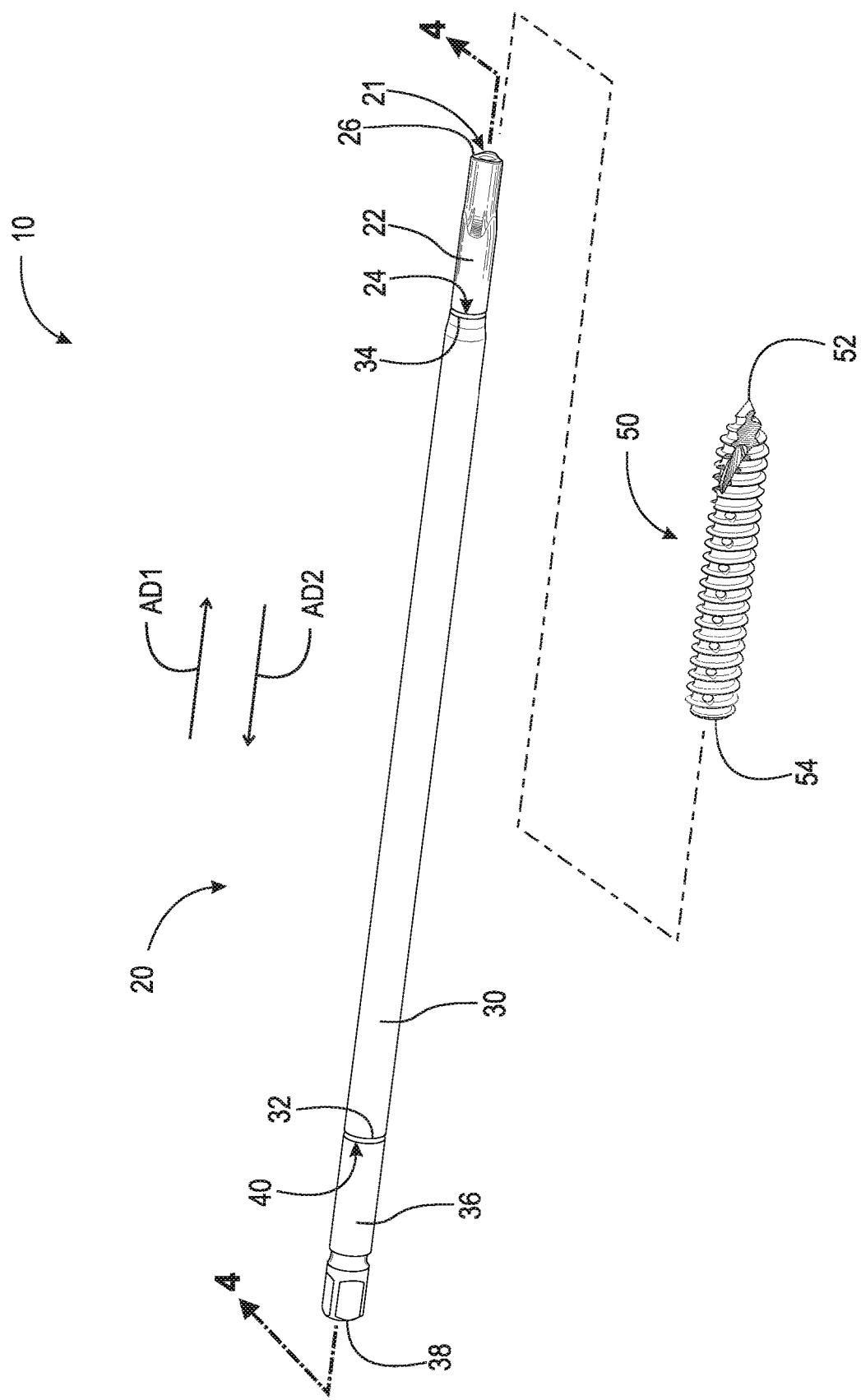
FIG. 2 is a front exploded perspective view of the fusion device assembly shown in FIG. 1.

Adverting now to the figures, FIG. 1 is a front perspective view of fusion device assembly 10. FIG. 2 is a front exploded perspective view of fusion device assembly 10. Fusion device assembly 10 generally comprises shaft 20 and fusion device 50. It should be appreciated that fusion devices 150 and 250 are also compatible with shaft 20 and may form fusion device assembly 10 along therewith. Shaft 20 is operatively arranged to drive fusion device 50 (and fusion devices 150 and 250) into a joint and allow graft material to be injected therein, as will be described in greater detail below.

FIG. 3 is a front perspective view of a section of shaft 20. FIG. 4 is a cross-sectional view of shaft 20 taken generally along line 4-4 in FIG. 2. The following description should be read in view of FIGS. 1-4.

Shaft 20 generally comprises through-bore 21, end 26, and end 32. Through-bore 21 extends from end 26 through end 32. In some embodiments, through-bore 21 extends from end 26 through end 38. In some embodiments, shaft 20 comprises one or more sections (e.g., sections 22, 30, and 36).

Section 22 is generally cylindrical and comprises end 24 and end 26. End 26 includes a coupler to non-rotatably connect shaft 20 to fusion device 50, 150, 250. For example, end 26 may comprise coupling lobes 28A-C that engage coupling lobes 56A-C in fusion device 50, similar to a socket connection, to non-rotatably connect shaft 20 and fusion device 50. In some embodiments, section 22 is removably connected to section 30, such that various coupler sizes or geometries may be assembled on shaft 20.

Section 30 is generally cylindrical and comprises end 32 and end 34. End 34 is arranged to engage end 24 to non-rotatably connect sections 22 and 30. End 32 is arranged to engage end 40 to non-rotatably connect sections 30 and 36.

Section 36 comprises end 38 and end 40. In some embodiments, section 36 is a hollow cylinder. In such embodiments, bone graft material can be inserted into end 38 and injected into fusion device 50, 150, 250 through through-bore 21. In some embodiments, section 36 is solid and is removably connected to section 30. In such embodiments, section 36 can be removed from section 30 such that bone graft material can be inserted into end 32 and injected into fusion device 50, 150, 250 through through-bore 21. End 40 is arranged to engage end 32 to non-rotatably connect sections 30 and 36. End 38 may comprise a universal coupler for connection to tool 12 (see FIGS. 17-18), for example, a power drill, torque handle, ratcheting T-handle, etc. In some embodiments, end 38 is a universal hex bit. In some embodiments, end 38 is a universal square bit.

Shaft 20 is specifically designed to circumferentially drive fusion device 50, 150, 250 into a joint. Once fusion device 50, 150, 250 is properly implanted, bone graft material is then injected into fusion device 50, 150, 250 through shaft 20, specifically through through-bore 21. As previously described, in some embodiments, section 36 is first removed to inject bone material through shaft 20. A plunger or a ram rod may be employed to force the bone graft material through shaft 20 and into fusion device 50, 150, 250. For example, a small rod having a diameter that is less than the diameter of through-bore 21 may be inserted into through-bore 21, after the bone graft material, to inject or pack the bone graft material into fusion device 50, 150, 250, similar to a ram rod of a musket. In some embodiments, bone material is inserted into shaft 20 through end 38. It should be appreciated that in some embodiments, shaft 20 is a single element (i.e., sections 22, 30, and 36 are integrally formed).

Figure 5A:
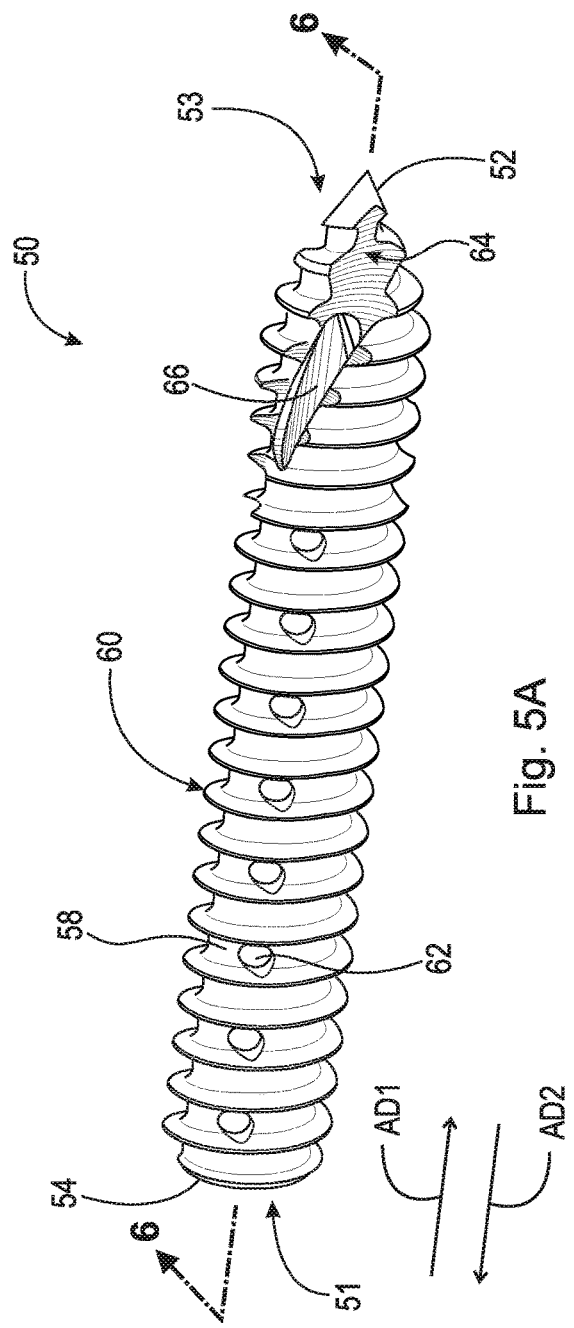
FIG. 5A is a front perspective view of the fusion device shown in FIG. 1.
Figure 5B:
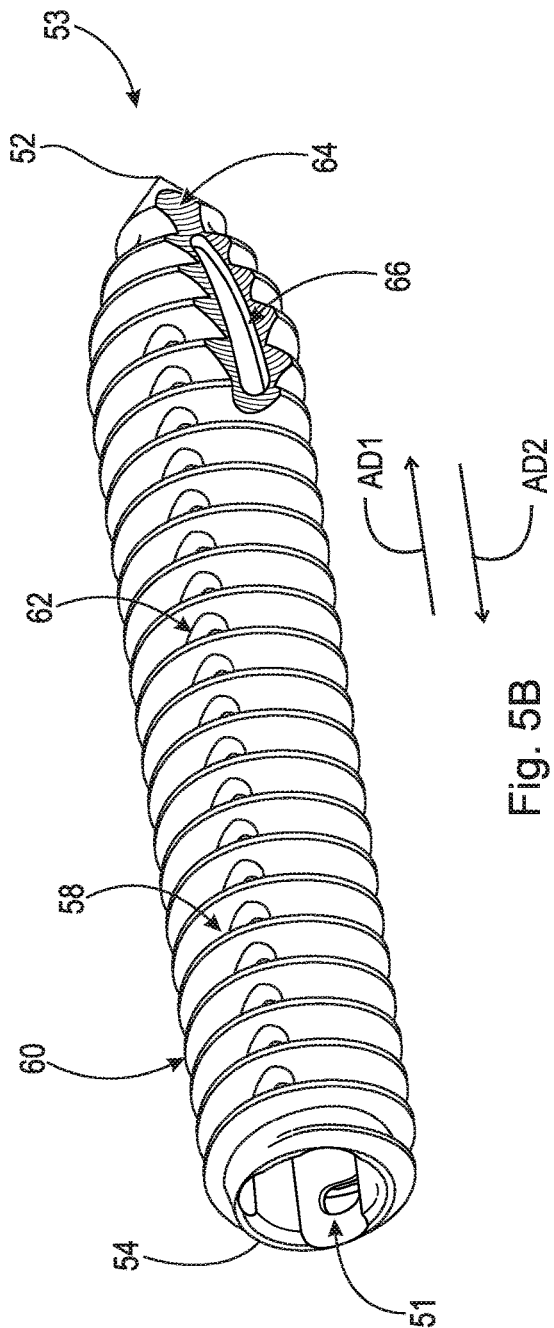
FIG. 5B is a rear perspective view of the fusion device shown in FIG. 1.
Figure 5C:
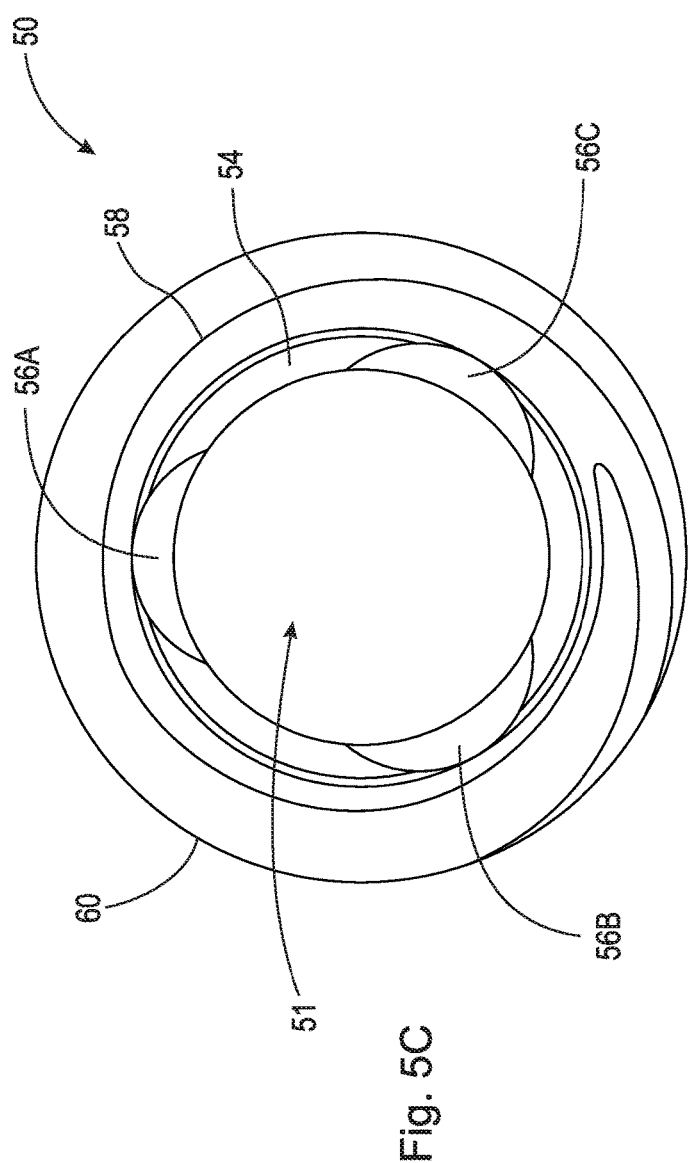
FIG. 5C is a rear elevational view of the fusion device shown in FIG. 1.
Figure 6:
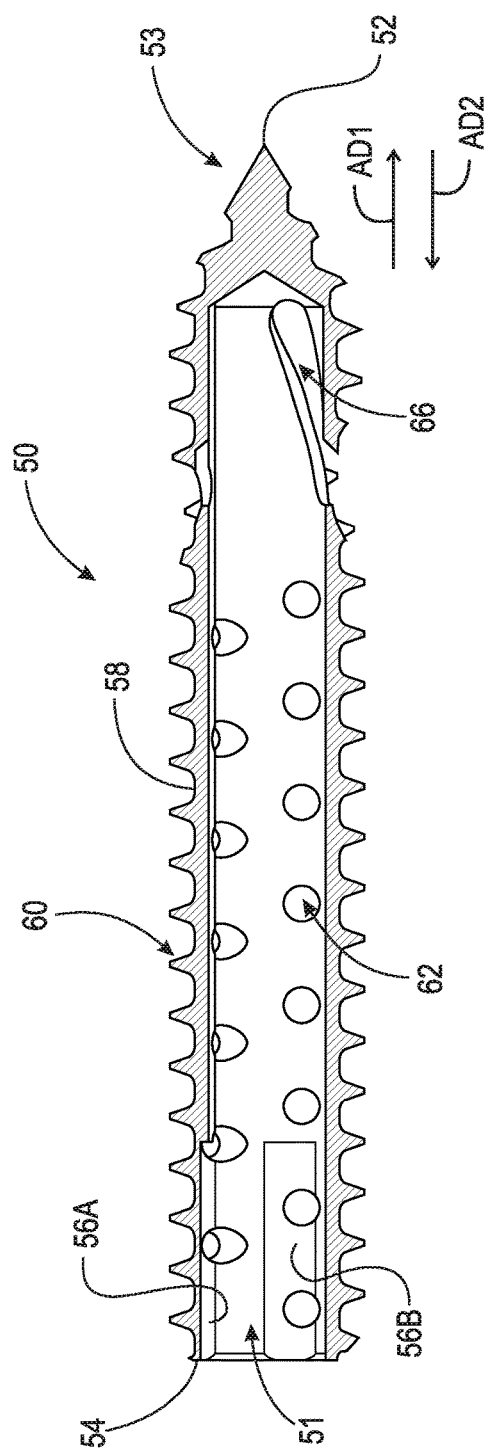

FIG. 5A is a front perspective view of fusion device 50. FIG. 5B is a rear perspective view of fusion device 50. FIG. 5C is a rear elevational view of fusion device 50. FIG. 6 is a cross-sectional view of fusion device 50 taken generally along line 6-6 in FIG. 5A. Fusion device 50 generally comprises bore 51, end 52, end 54, and radially outward facing surface 58. The following description should be read in view of FIGS. 1-6.

Fusion device 50 is generally cylindrical and is operatively arranged to engage a joint. Fusion device 50 is a self-boring, self-tapping, fusion screw. In some embodiments, fusion device 50 is hollow and self-harvesting (i.e., harvests bone). As shown, fusion device 50 comprises a twist bit, a multi-purpose bit, or a pilot point bit having a cutting point/tip/edge, i.e., drill bit 53, at end 52, which comprises one or more flutes 64. Flutes 64 may comprise one or more cutting edges. In some embodiments, end 52 comprises a Brad point bit, a Forstner bit, or a spade bit. End 52 and flutes 64 are operatively arranged to bore a hole through the joint, specifically through the bone. Fusion device 50 further comprises one or more apertures 66 formed adjacent to flutes 64. Flutes 64 and apertures 66 work in conjunction such that as fusion device 50 is being driven into the joint, bone is removed from the joint by the tip at end 52 and flutes 64 and forced into bore 51 via apertures 66. The removed bone that is forced into bore 51 aids in the fusion of the joint. Bore 51 extends substantially through fusion device 50. Specifically, bore 51 extends from end 54 to proximate end 52. Apertures 66 extend from radially outward facing surface 58 radially inward to bore 51. End 54 includes a coupler to non-rotatably connect shaft 20 to fusion device 50. For example, end 54 may comprise coupling lobes 56A-C that engage coupling lobes 28A-C in shaft 20, similar to a socket connection, to non-rotatably connect shaft 20 and fusion device 50 (see FIG. 5C). Radially outward facing surface 58 further comprises threading 60. Threading 60 is designed not only to secure the joint (two bones) together, but also to tap the hole bored out in the joint by end 52 (the drill tip) and flutes 64. In some embodiments, threading 60 comprises a varying pitch such that compression occurs gradually across the joint as fusion device 50 advances therein. In some embodiments, radially outward facing surface 58 comprises threading from end 52 to end 54 (i.e., fusion device 50 is fully threaded). In some embodiments, radially outward facing surface 58 is partially threaded. For example, threads and flutes are found proximate end 52 followed by a non-threaded middle section and then smaller pitched threads proximate end 54 to facilitate joint compression in the manner of a lag-screw. In some embodiments, fusion device 50 is a fully threaded regular pitch bone screw. Radially outward facing surface 58 further comprises a plurality of apertures 62. Apertures 62 extend from radially outward facing surface 58 radially inward to bore 51 and allow for the removed bone material residing in bore 51 (i.e., the bone material fed into bore 51 through apertures 66) to engage with the joint such that, over time, joint fusion occurs. Apertures 62 further allow for bone graft material injected into fusion device 50 through shaft 20 to engage the joint for joint fusion. In other words, apertures 62 allow for bony in-growth and through growth/fusion. It should be appreciated that apertures 62 may comprise any geometric shape suitable to allow fusion to occur between graft residing within bore 51 and the joint (e.g., circular, ovular, triangular, square, rectangular, etc.).

Figure 7:
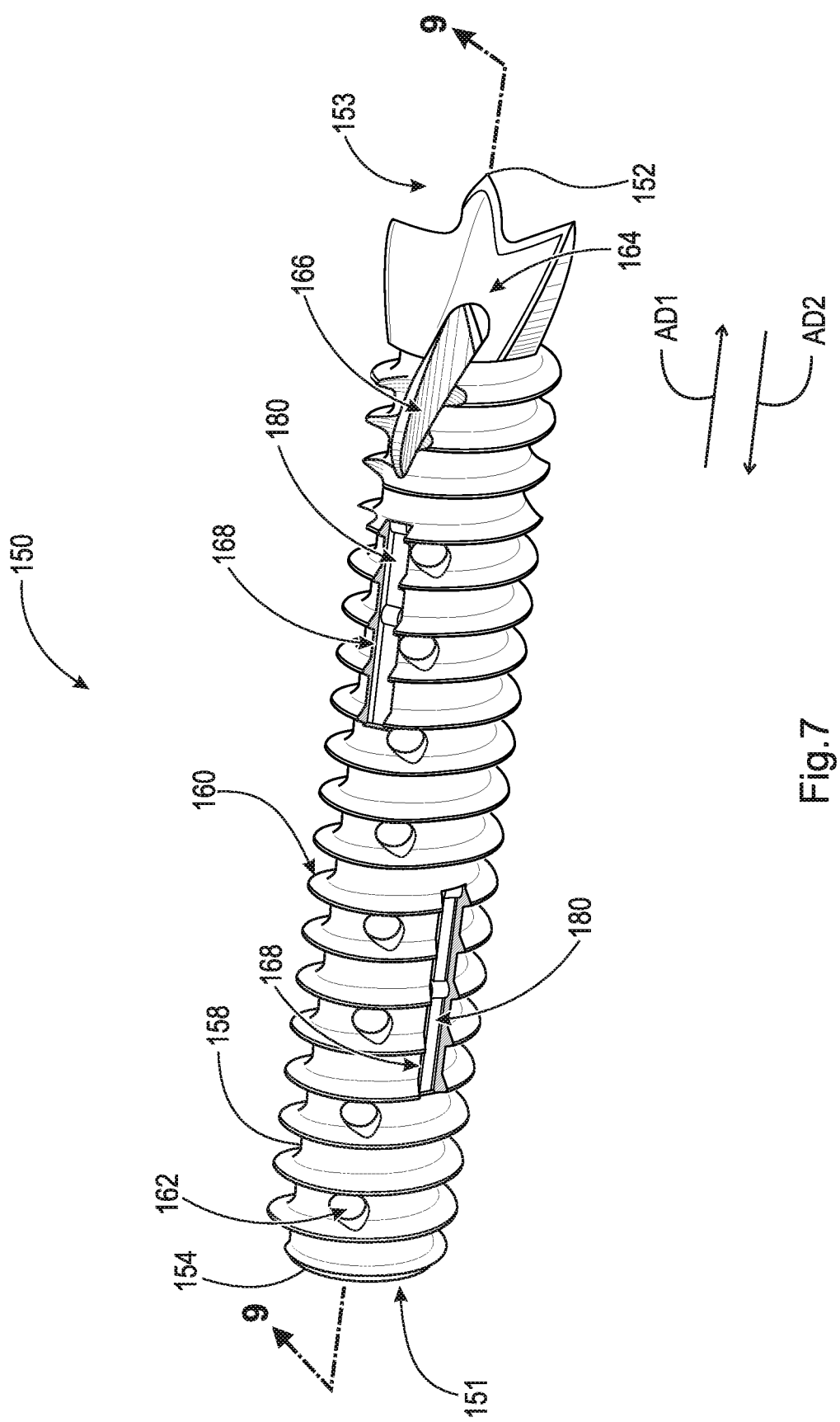
FIG. 7 is a front perspective view of a fusion device, in an unexpanded state.
Figure 8:
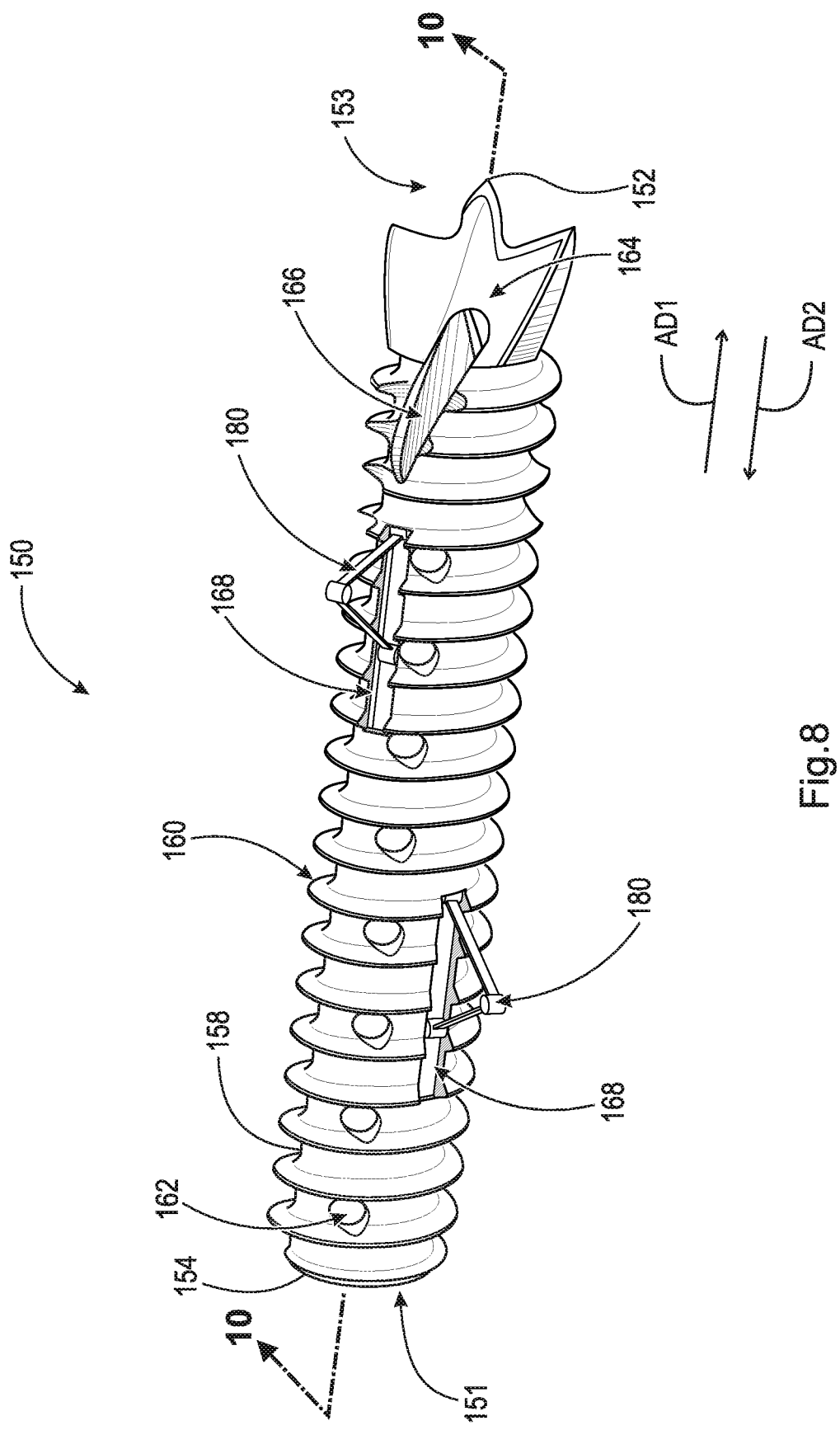
FIG. 8 is a front perspective view of the fusion device shown in FIG. 7, in an expanded state.
Figure 9:
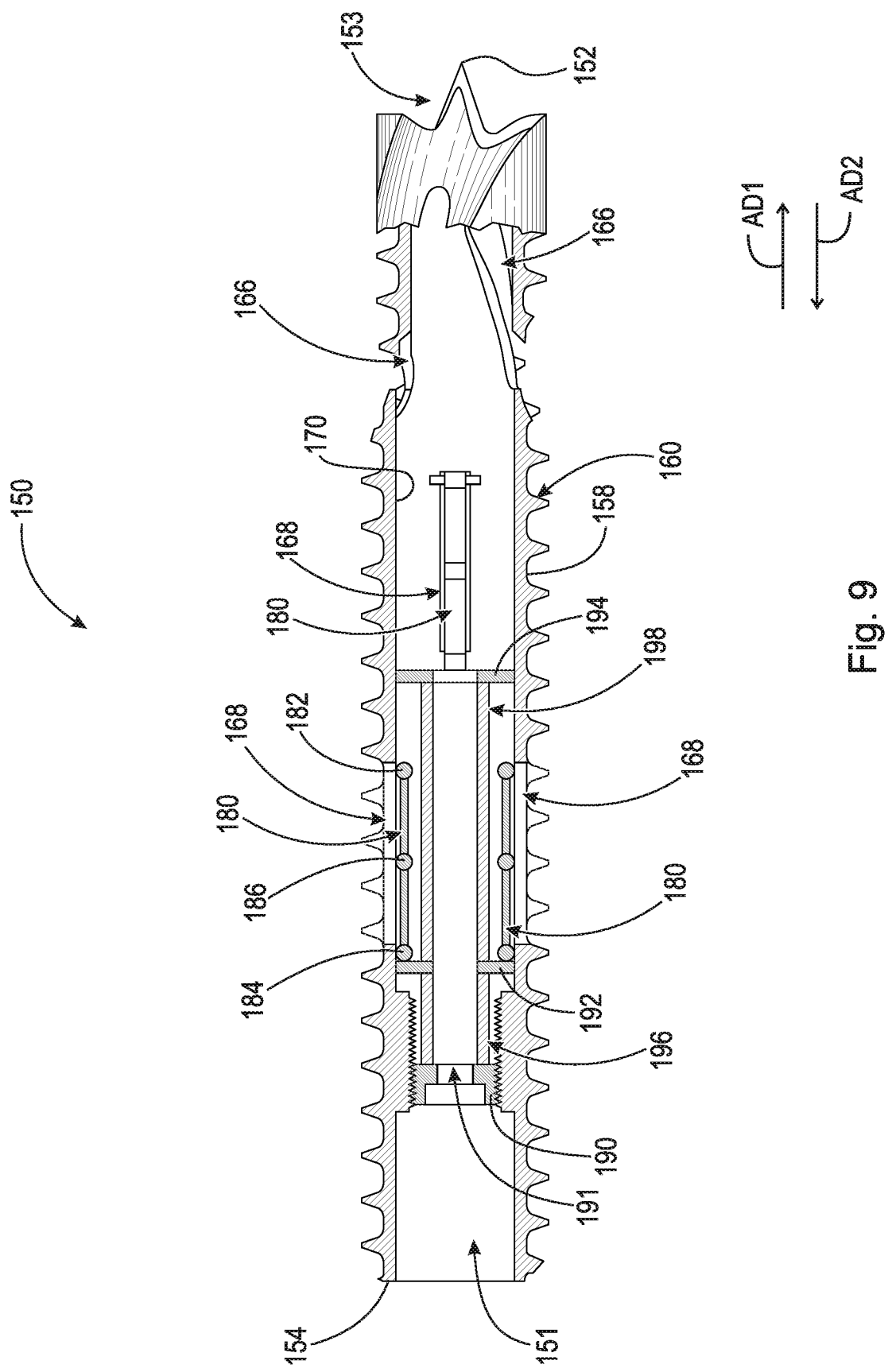
FIG. 9 is a cross-sectional view of the fusion device, in the unexpanded state, taken generally along line 9-9 in FIG. 7.
Figure 10:
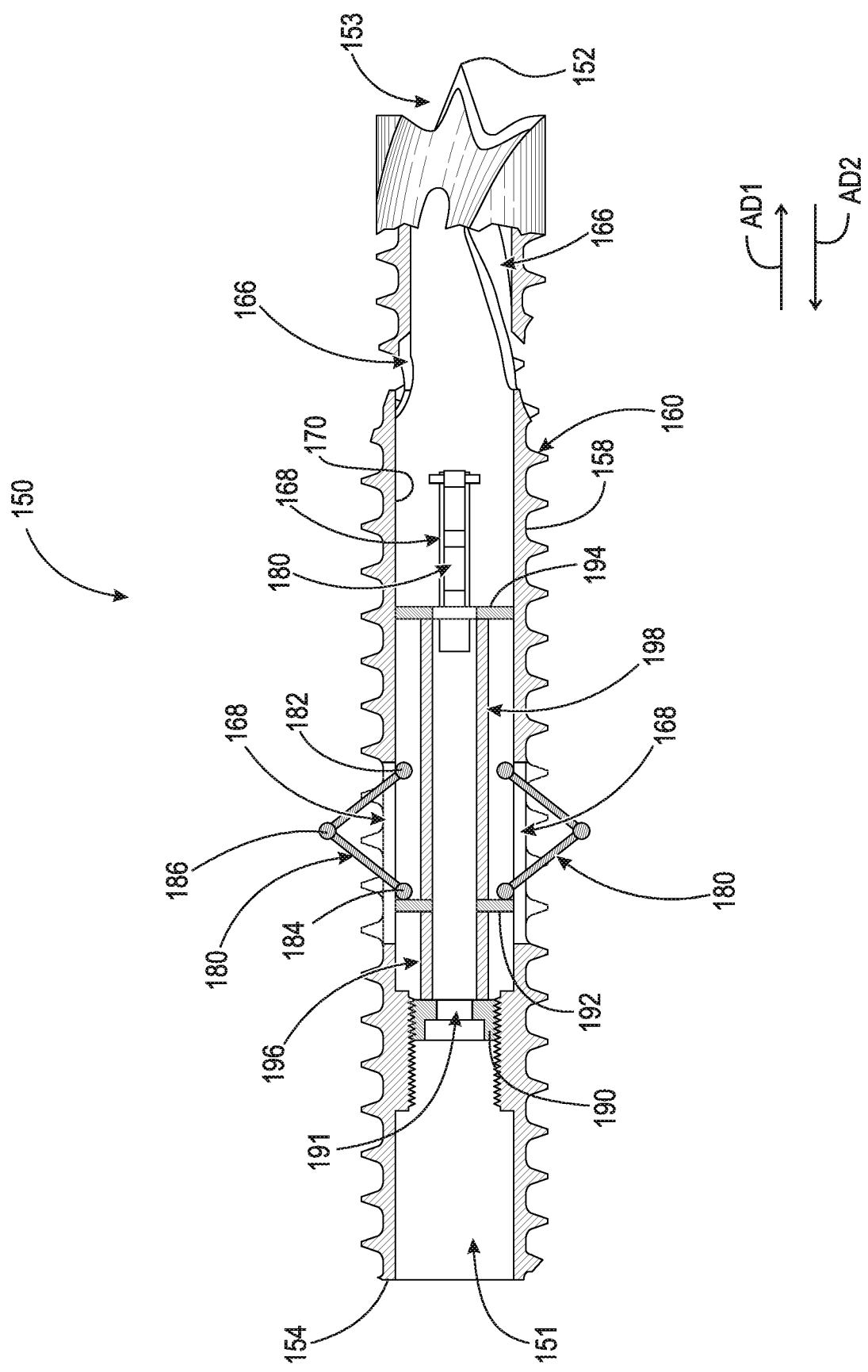
FIG. 10 is a cross-sectional view of the fusion device, in the expanded state, taken generally along line 10-10 in FIG. 8.
Figure 11:
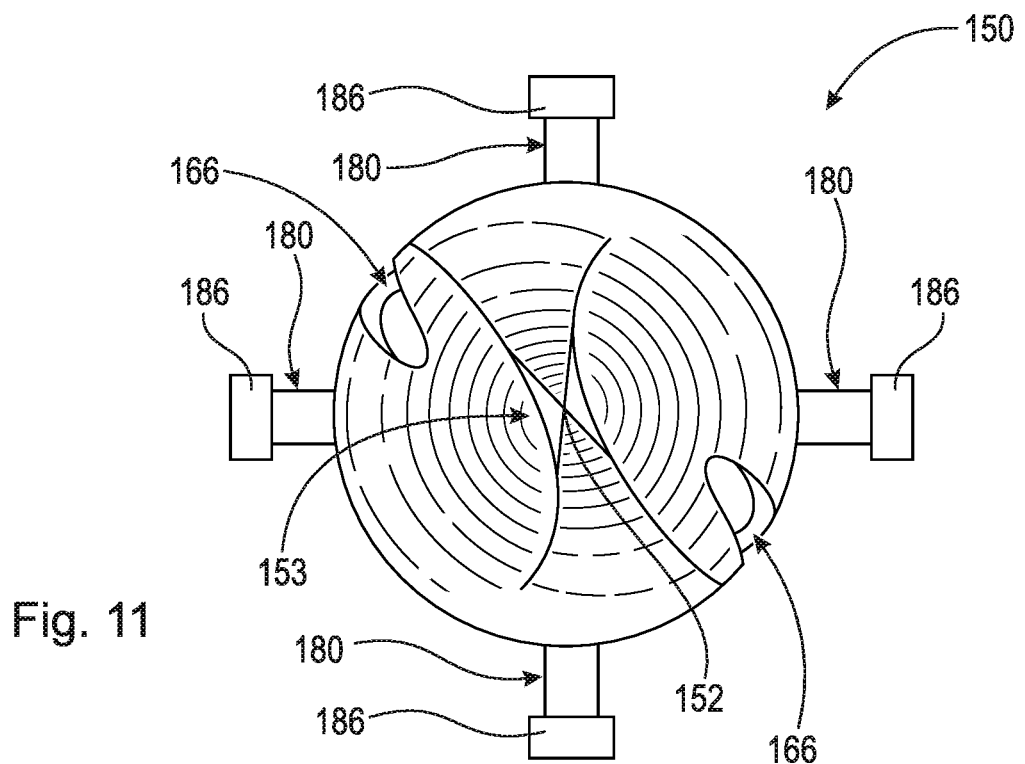
FIG. 11 is a front elevational view of the fusion device, in the expanded state, shown in FIG. 8.
Figure 12:
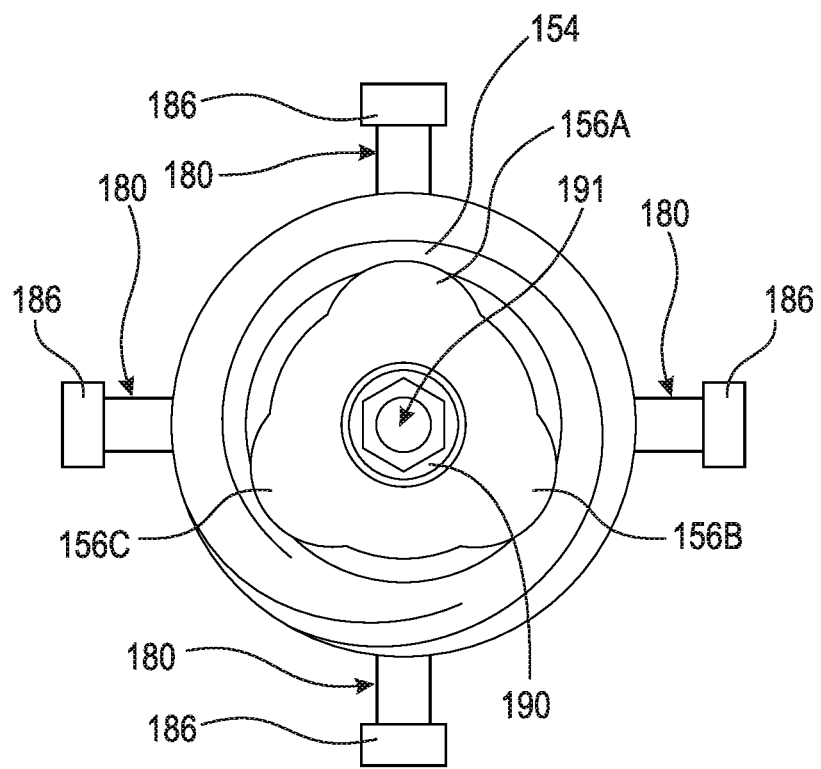
FIG. 12 is a rear elevational view of the fusion device, in the expanded state, shown in FIG. 8.

FIG. 7 is a front perspective view of fusion device 150, in an unexpanded state. FIG. 8 is a front perspective view of fusion device 150, in an expanded state. FIG. 9 is a cross-sectional view of fusion device 150, in the unexpanded state, taken generally along line 9-9 in FIG. 7. FIG. 10 is a cross-sectional view of fusion device 150, in the expanded state, taken generally along line 10-10 in FIG. 8. FIG. 11 is a front elevational view of fusion device 150, in the expanded state. FIG. 12 is a rear elevational view of fusion device 150, in the expanded state. Fusion device 150 generally comprises bore 151, end 152, end 154, and radially outward facing surface 158. The following description should be read in view of FIGS. 1-4 and 7-12.

Fusion device 150 is generally cylindrical and is operatively arranged to engage a joint. Fusion device 150 is a self-boring, self-tapping, fusion screw. In some embodiments, fusion device 150 is hollow and self-harvesting (i.e., harvests bone). As shown, fusion device 150 comprises a Brad point bit having a cutting point/tip/edge, i.e., drill bit 153, at end 152, which comprises one or more flutes 164. Flutes 164 may comprise one or more cutting edges. In some embodiments, end 152 comprises a twist bit, a multi-purpose bit, a pilot point bit, a Forstner bit, or a spade bit. End 152 and flutes 164 are operatively arranged to bore a hole through the joint, specifically through the bone. Fusion device 150 further comprises one or more apertures 166 formed adjacent to flutes 164. Flutes 164 and apertures 166 work in conjunction such that as fusion device 150 is being driven into the joint, bone is removed from the joint by the tip at end 152 and flutes 164 and forced into bore 151 via apertures 166. The removed bone that is forced into bore 151 aids in the fusion of the joint. Bore 151 extends substantially through fusion device 150. Specifically, bore 151 extends from end 154 to proximate end 152. Apertures 166 extend from radially outward facing surface 158 radially inward to bore 151. End 154 includes a coupler to non-rotatably connect shaft 20 to fusion device 150. For example, end 154 may comprise coupling lobes 156A-C that engage coupling lobes 28A-C in shaft 20, similar to a socket connection, to non-rotatably connect shaft 20 and fusion device 150 (see FIG. 12). Radially outward facing surface 158 further comprises threading 160. Threading 160 is designed not only to secure the joint (two bones) together, but also to tap the hole bored out in the joint by end 152 (the drill tip) and flutes 164. In some embodiments, threading 160 comprises a varying pitch such that compression occurs gradually across the joint as fusion device 150 advances therein. In some embodiments, radially outward facing surface 158 comprises threading from end 152 to end 154 (i.e., fusion device 150 is fully threaded). In some embodiments, radially outward facing surface 158 is partially threaded. For example, threads and flutes are found proximate end 152 followed by a non-threaded middle section and then smaller pitched threads proximate end 154 to facilitate joint compression in the manner of a lag-screw. In some embodiments, fusion device 150 is a fully threaded regular pitch bone screw. Radially outward facing surface 158 further comprises a plurality of apertures 162. Apertures 162 extend from radially outward facing surface 158 radially inward to bore 151 and allow for the removed bone material residing in bore 151 (i.e., the bone material fed into bore 151 through apertures 166) to engage with the joint such that, over time, joint fusion occurs. Apertures 162 further allow for bone graft material injected into fusion device 150 through shaft 20 to engage the joint for joint fusion. In other words, apertures 162 allow for bony in-growth and through growth/fusion. It should be appreciated that apertures 162 may comprise any geometric shape suitable to allow fusion to occur between graft residing within bore 151 and the joint (e.g., circular, ovular, triangular, square, rectangular, etc.).

Fusion device 150 further comprises one or more expandable members 180 operatively arranged to expand radially outward through one or more openings 168 from bore 151 and engage the bone(s) of the joint. As shown openings 168 are arranged in radially outward facing surface 158 and extend radially inward to bore 151. In some embodiments, expandable members 180 comprise pivots 182, 184, and 186. For example, pivot 182 may be fixedly secured to radially inward facing surface 170 and pivot 184 may be slidably connected to radially inward facing surface. As sliding pivot 184 is displaced in axial direction AD1, pivot 186 expands radially outward through openings 168 (see FIGS. 9-10). As expandable members 180 (e.g., radially expanding pivots 186) expand radially outward, they engage the joint or bones of the joint and prevent fusion device 150 from disengaging the joint (i.e., from unscrewing from the joint), and also serves to stabilize proximate elements of the bones or joint such that excess motion which may hinder fusion is thereby mitigated.

In some embodiments fusion device 150 further comprises nut 190 and one or more plates (e.g., plates 192 and 194) operatively arranged to displace pivot 184 in axial direction AD1 such that expandable members 180 expand radially through openings 168. Nut 190 is threadably engaged with radially inward facing surface 170 and comprises through-bore 191. Nut 190 is connected to plate 192 and/or plate 194 via one or more connectors 196 and/or one or more connectors 198, respectively. In some embodiments, nut 190 is non-rotatably connected to plate 192 and/or plate 194. In some embodiments, nut 190 is rotatably connected to plate 192 and/or plate 194. Plate 192 and plate 194 are operatively arranged to engage or abut against sliding pivots 184 to displace sliding pivots 184 in axial direction AD1. In some embodiments, nut 190 directly engages or abuts against sliding pivot 184 without the need for plates or connectors. Once fusion device 150 is properly implanted in a joint, shaft 20 is removed from end 154 and a tool (e.g., screwdriver, Allen wrench, socket, etc.) is inserted into nut 190. Nut 190 is rotated such that nut 190 is displaced in axial direction AD1 relative to end 154. This causes plates 192 and 194 and sliding pivots 184 to displace in axial direction AD1, which forces expandable members 180 radially outward through openings 168 to engage the bones of the joint. Through-bore 191 allows bone graft material to be injected into fusion device 150 through end 154 via shaft 20. In some embodiments, plate 192 comprises a through-bore. In some embodiments, plate 194 comprises a through-bore. In some embodiments, plate 192 and/or plate 194 is threadably engaged with radially inward facing surface 170.

Figure 13:
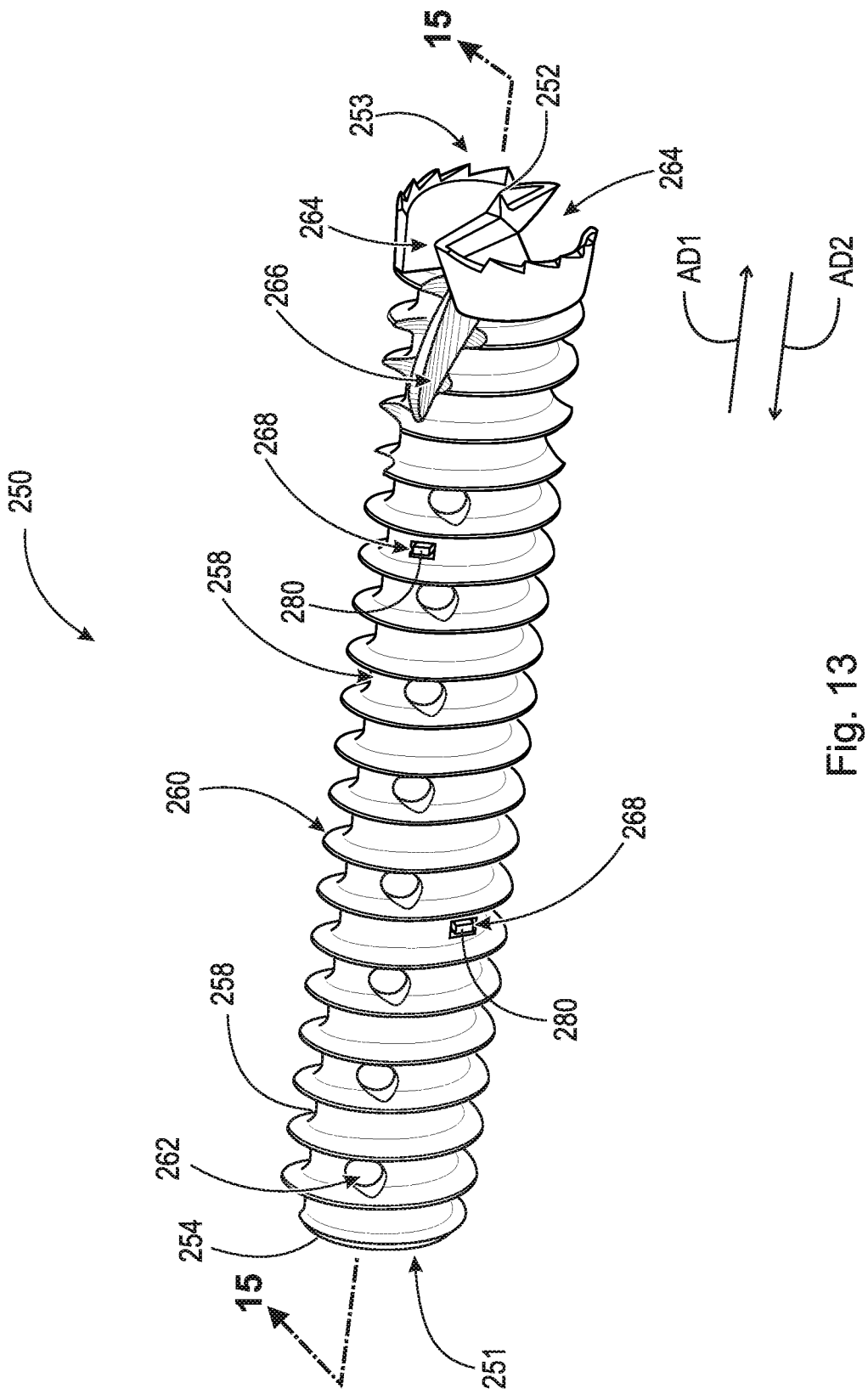
FIG. 13 is a front elevational view of a fusion device, in an unexpanded state.
Figure 14:
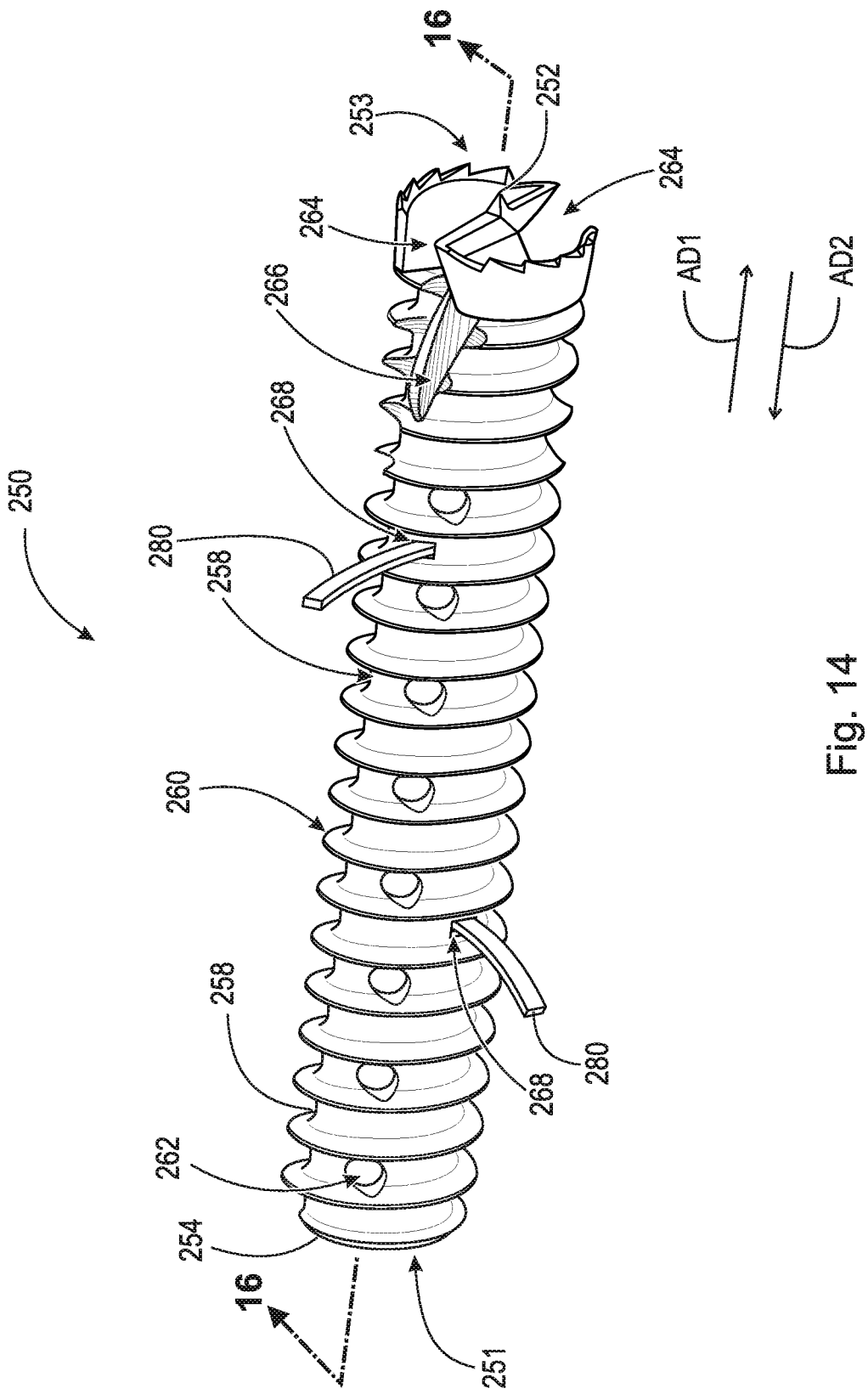
FIG. 14 is a front elevational view of the fusion device shown in FIG. 13, in an expanded state.
Figure 15:
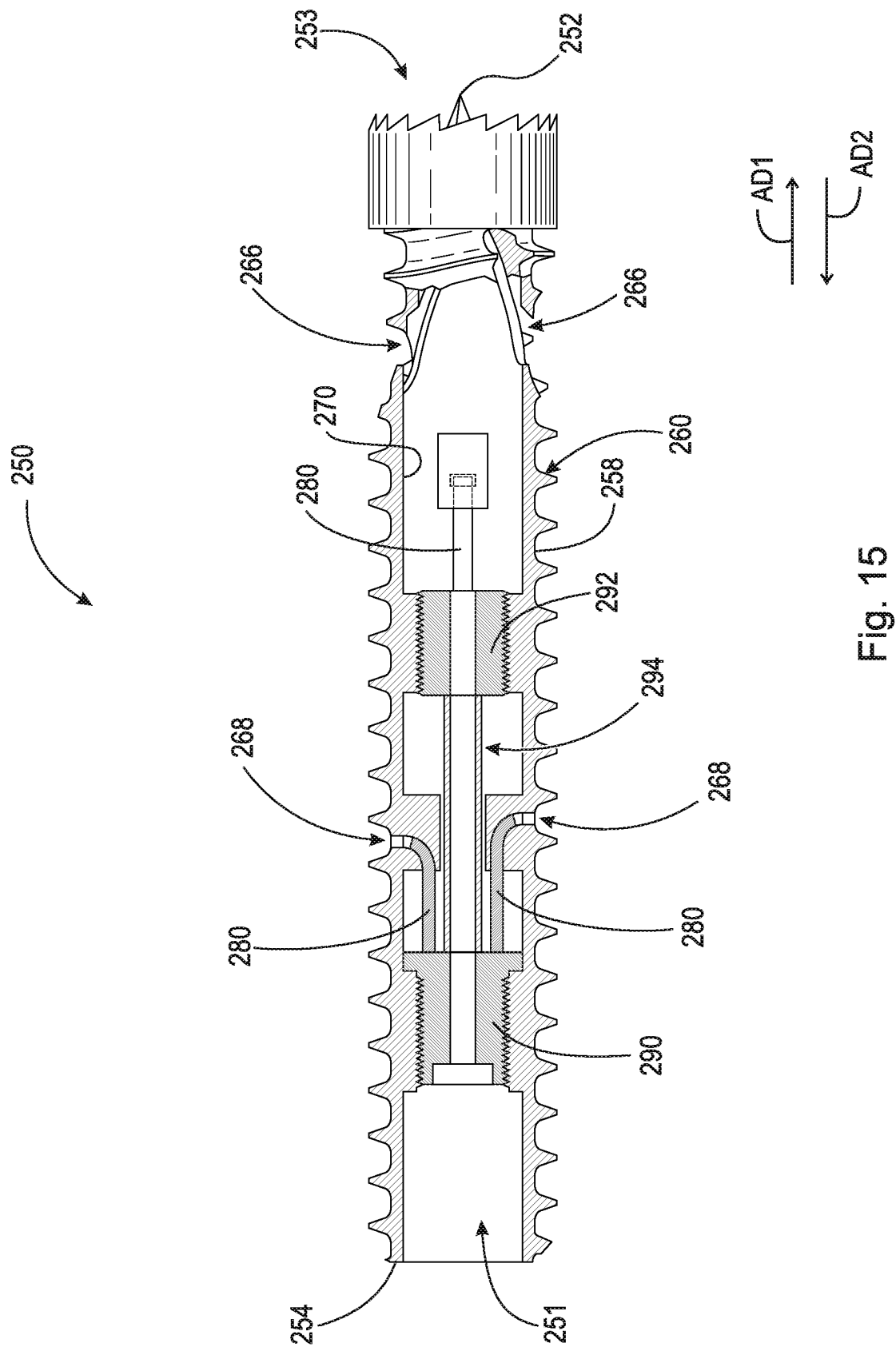
FIG. 15 is a cross-sectional view of the fusion device, in the unexpanded state, taken generally along line 15-15 in FIG. 13.
Figure 16:
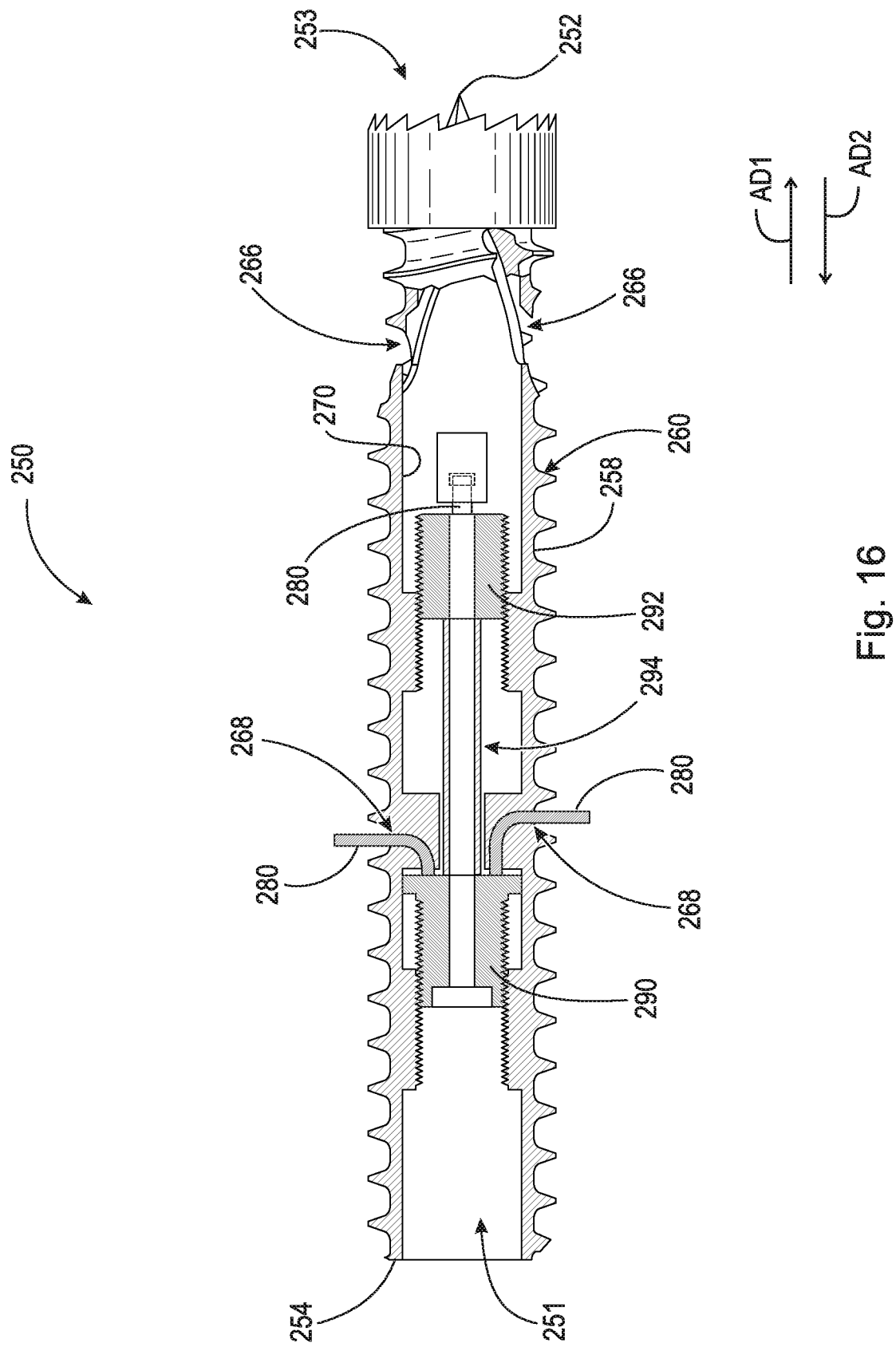
FIG. 16 is a cross-sectional view of the fusion device, in the expanded state, taken generally along line 16-16 in FIG. 14.

FIG. 13 is a front elevational view of fusion device 250, in an unexpanded state. FIG. 14 is a front elevational view of fusion device shown 250, in an expanded state. FIG. 15 is a cross-sectional view of fusion device 250, in the unexpanded state, taken generally along line 15-15 in FIG. 13. FIG. 16 is a cross-sectional view of fusion device 250, in the expanded state, taken generally along line 16-16 in FIG. 14. Fusion device 250 generally comprises bore 251, end 252, end 254, and radially outward facing surface 258. The following description should be read in view of FIGS. 1-4 and 13-16.

Fusion device 150 is generally cylindrical and is operatively arranged to engage a joint. Fusion device 250 is a self-boring, self-tapping, fusion screw. In some embodiments, fusion device 250 is hollow and self-harvesting (i.e., harvests bone). As shown, fusion device 250 comprises a Forstner bit having a cutting point/tip/edge, i.e., drill bit 253, at end 252, which comprises one or more flutes 264. Flutes 264 may comprise one or more cutting edges. In some embodiments, end 252 comprises a twist bit, a multi-purpose bit, a pilot point bit, a Brad point bit, or a spade bit. End 252 and flutes 264 are operatively arranged to bore a hole through the joint, specifically through the bone. Fusion device 250 further comprises one or more apertures 266 formed adjacent to flutes 264. Flutes 264 and apertures 266 work in conjunction such that as fusion device 250 is being driven into the joint, bone is removed from the joint by the tip at end 252 and flutes 264 and forced into bore 251 via apertures 266. The removed bone that is forced into bore 251 aids in the fusion of the joint. Bore 251 extends substantially through fusion device 250. Specifically, bore 251 extends from end 254 to proximate end 252. Apertures 266 extend from radially outward facing surface 258 radially inward to bore 251. End 254 includes a coupler to non-rotatably connect shaft 20 to fusion device 250. For example, end 254 may comprise coupling lobes 256A-C (not shown) that engage coupling lobes 28A-C in shaft 20, similar to a socket connection, to non-rotatably connect shaft 20 and fusion device 250. Radially outward facing surface 258 further comprises threading 260. Threading 260 is designed not only to secure the joint (two bones) together, but also to tap the hole bored out in the joint by end 252 (the drill tip) and flutes 264. In some embodiments, threading 260 comprises a varying pitch such that compression occurs gradually across the joint as fusion device 250 advances therein. In some embodiments, radially outward facing surface 258 comprises threading from end 252 to end 254 (i.e., fusion device 250 is fully threaded). In some embodiments, radially outward facing surface 258 is partially threaded. For example, threads and flutes are found proximate end 252 followed by a non-threaded middle section and then smaller pitched threads proximate end 254 to facilitate joint compression in the manner of a lag-screw. In some embodiments, fusion device 250 is a fully threaded regular pitch bone screw. Radially outward facing surface 258 further comprises a plurality of apertures 262. Apertures 262 extend from radially outward facing surface 258 radially inward to bore 251 and allow for the removed bone material residing in bore 251 (i.e., the bone material fed into bore 251 through apertures 266) to engage with the joint such that, over time, joint fusion occurs. Apertures 262 further allow for bone graft material injected into fusion device 250 through shaft 20 to engage the joint for joint fusion. In other words, apertures 262 allow for bony in-growth and through growth/fusion. It should be appreciated that apertures 262 may comprise any geometric shape suitable to allow fusion to occur between graft residing within bore 251 and the joint (e.g., circular, ovular, triangular, square, rectangular, etc.).

Fusion device 250 further comprises one or more expandable members 280 operatively arranged to extend radially outward through one or more openings 268 from bore 251 and engage the bone(s) of the joint. As shown openings 268 are arranged in radially outward facing surface 258 and extend radially inward to bore 251. In some embodiments, expandable members 280 are flexible structures that can be fed along a curved path (FIGS. 15-16). As one end of expandable member 280 is displaced in axial direction AD1, the other end of expandable member 280 is curved radially outward from radially outward facing surface. As expandable members 280 extend radially outward, they engage the joint or bones of the joint and prevent fusion device 250 from disengaging the joint (i.e., from unscrewing from the joint).

In some embodiments fusion device 250 further comprises nut 290 and one or more plates (e.g., plate 292) operatively arranged to displace one end of expandable members 280 in axial direction AD1 such that the other end of expandable members 280 extends radially through openings 268. Nut 290 is threadably engaged with radially inward facing surface 270 and comprises through-bore 291. Nut 290 is connected to plate 292 via one or more connectors 294. In some embodiments, nut 290 is non-rotatably connected to plate 292. In some embodiments, nut 290 is rotatably connected to plate 292. Nut 290 and/or plate 292 is operatively arranged to engage or abut against expandable members 280 to displace expandable members 280 in axial direction AD1 (and subsequently radially outward from radially outward facing surface 258). In some embodiments, and as shown in FIGS. 15 and 16, nut 290 directly engages or abuts against expandable members 280. Once fusion device 250 is properly implanted in a joint, shaft 20 is removed from end 254 and a tool (e.g., screwdriver, Allen wrench, socket, etc.) is inserted into nut 290. Nut 290 is rotated such that nut 290 is displaced in axial direction AD1 relative to end 254. This causes plate 292 and one end of expandable members 280 to displace in axial direction AD1, which forces the other end of expandable members 280 radially outward through openings 268 to engage the bones of the joint. Through-bore 291 allows bone graft material to be injected into fusion device 250 through end 254 via shaft 20. In some embodiments, plate 292 comprises a through-bore. In some embodiments, plate 292 is threadably engaged with radially inward facing surface 270.

Figure 17:
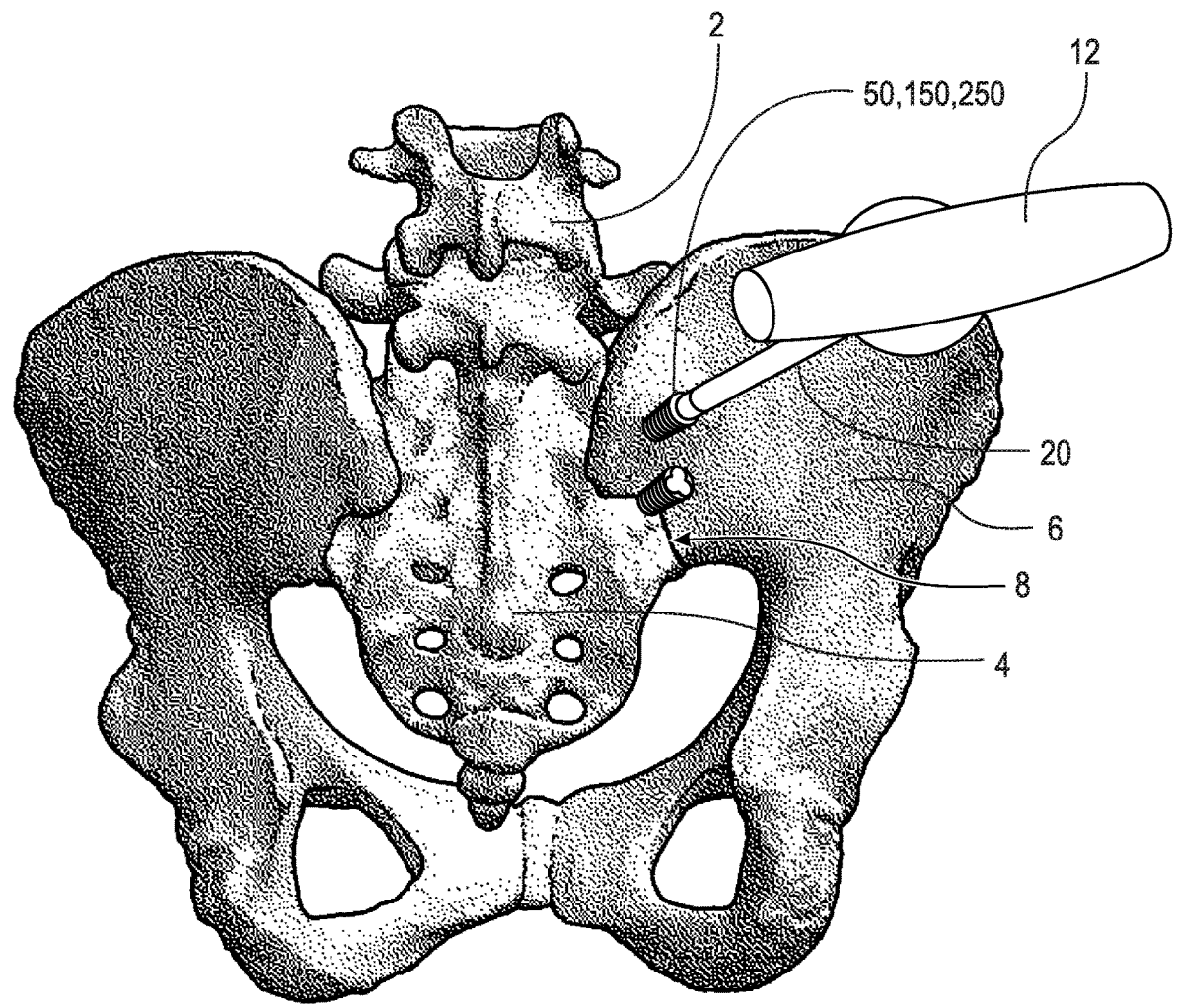
FIG. 17 is a posterior view of a fusion device being implanted in a sacroiliac joint; and, FIG. 18 is a lateral view of the fusion device being implanted in the sacroiliac joint, as shown in FIG. 17.
Figure 18:
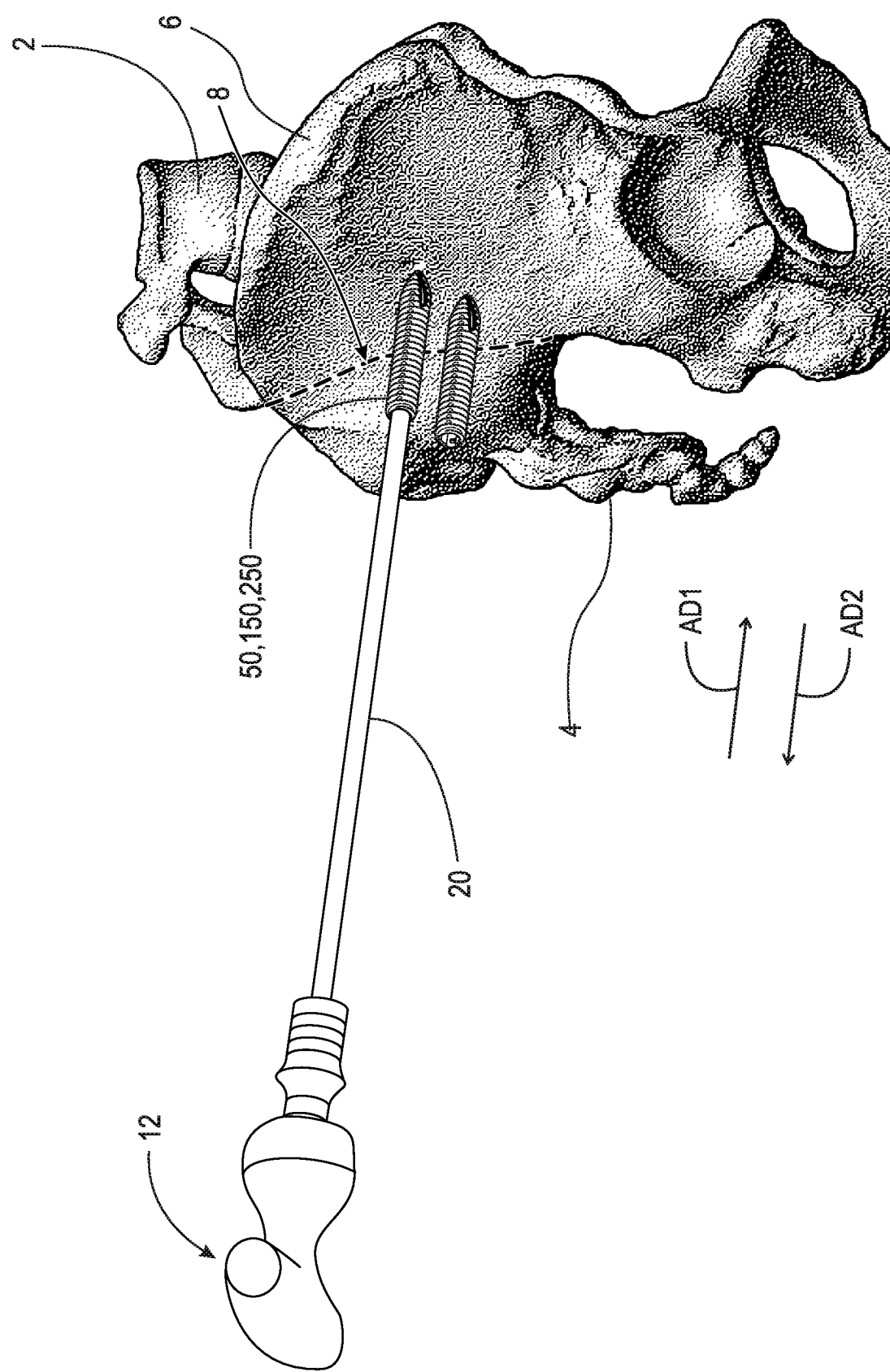

FIG. 17 is a posterior view of fusion device 50, 150, 250 being implanted in sacroiliac joint 8. FIG. 18 is a lateral view of fusion device 50, 150, 250 being implanted in sacroiliac joint 8. As shown, sacroiliac joint 8 comprises sacrum 4 and ilium 6. Sacrum 4 is connected to spinal column 2. Sacroiliac joint 8 is the connection between spinal column 2 and the pelvis. Fusion device 50, 150, 250 is implanted into sacroiliac joint 8 and once properly arranged, extends from ilium 6 to sacrum 4. As previously described, the threading of fusion device 50, 150, 250 is operatively arranged to pull ilium 6 and sacrum 4 together (i.e., into compression). Fusion device 50, 150, 250 is driven into sacroiliac joint 8 via shaft 20 and tool 12. In some embodiments, once fusion device 50, 150, 250 is in place, tool 12 is removed from shaft 20 and bone material is injected into fusion device 50, 150, 250 through shaft 20. Shaft 20 is then removed from fusion device 50, 150, 250 and the wound is closed. In some embodiments, shaft 20 is removed and expandable members within the fusion device (e.g., fusion device 150, 250) are expanded radially outward. For example, in fusion device 150, nut 190 is rotated such that expandable members 180 extend radially outward from radially outward surface 158 and engage sacrum 4 and/or ilium 6. In fusion device 250, nut 290 is rotated such that expandable members 280 extend radially outward from radially outward surface 258 and engage sacrum 4 and/or ilium 6. After radial expansion of fusion device 150, 250, shaft 20 can be reconnected thereto and bone graft material injected therein. Fusion device 50, 150, 250 left in situ once filled with fusion material. Fusion device 50, 150, 250 is shown being implanted into sacroiliac joint 8 posteriorly; however, it should be appreciated that fusion device 50, 150, 250 may be implanted into sacroiliac joint 8 laterally.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMERALS

2 Spinal column
4 Sacrum
6 Ilium
8 Sacroiliac joint
10 Fusion device assembly
12 Tool
20 Shaft
21 Through-bore
22 Section
24 End
26 End
28A Coupling lobe
28B Coupling lobe
28C Coupling lobe
30 Section
32 End
34 End
36 Section
38 End
40 End
50 Fusion device
51 Bore
52 End
53 Cutting edge/blade/tip (or drill bit)
54 End
56A Coupling lobe
56B Coupling lobe
56C Coupling lobe
58 Radially outward facing surface
60 Threading
62 Aperture(s)
64 Flute(s)
66 Aperture(s)
150 Fusion device
151 Bore
152 End
153 Cutting edge/blade/tip (or drill bit)
154 End
156A Coupling lobe
156B Coupling lobe
156C Coupling lobe
158 Radially outward facing surface
160 Threading
162 Aperture(s)
164 Flute(s)
166 Aperture(s)
168 Opening(s)
170 Radially inward facing surface
180 Expandable member(s)
182 Fixed pivot
184 Sliding pivot
186 Radially expanding pivot
190 Nut
191 Through-bore
192 Plate
194 Plate
196 Connector(s)
198 Connector(s)
250 Fusion device
251 Bore
252 End
253 Cutting edge/blade/tip (or drill bit)
254 End
256A Coupling lobe (not shown)
256B Coupling lobe (not shown)
256C Coupling lobe (not shown)
258 Radially outward facing surface
260 Threading
262 Aperture(s)
264 Flute(s)
266 Aperture(s)
268 Opening(s)
270 Radially inward facing surface
280 Expandable member(s)
290 Nut
291 Through-bore
292 Nut or plate
294 Connector(s)
AD1 Axial direction
AD2 Axial direction

What is claimed is:

1. A fusion device assembly for fusion of a joint, comprising:
a fusion device, including:
a distal end;
a proximal end;
a radially outward facing surface including threading, wherein the threading is continuous from the distal end to the proximal end and varies in pitch;
a bore extending from the proximal end;
at least one flute arranged proximate the distal end; and,
at least one aperture arranged adjacent to the at least one flute.

2. The fusion device as recited in claim 1, wherein the fusion device further comprises a plurality of fusion apertures extending from the radially outward facing surface to the bore.

3. The fusion device as recited in claim 1, wherein the proximal end further comprises a coupler.

4. The fusion device as recited in claim 3, wherein the coupler comprises one or more coupling lobes.

5. The fusion device as recited in claim 1, further comprising a shaft, the shaft including:
a first end;
a second end operatively arranged to be non-rotatably connected to the proximal end; and,
a through-bore extending from the first end to the second end.

6. The fusion device as recited in claim 5, wherein the shaft is removably connected to the fusion device.

7. The fusion device as recited in claim 1, wherein the fusion device further comprises at least one expandable member arranged in the bore, the at least one expandable member operatively arranged to extend radially outward through at least one opening in the radially outward facing surface.

8. The fusion device as recited in claim 7, wherein the fusion device further comprises a radially inward facing surface and a nut operatively arranged to engage the at least one expandable member, the nut being threadably engaged with the radially inward facing surface.

9. The fusion device as recited in claim 8, wherein the at least one expandable member comprises:
a first pivot fixedly secured to the radially inward facing surface;
a second pivot slidably connected to the radially inward facing surface; and,
a third pivot, wherein when the first pivot is displaced in a first axial direction relative to the proximal end, the third pivot displaces radially outward from the radially outward facing surface.

10. The fusion device as recited in claim 8, wherein when the nut is displaced in a first axial direction relative to the proximal end, the at least one expandable member displaces radially outward from the radially outward facing surface.

11. The fusion device as recited in claim 7, wherein the at least one expandable member is flexible.

12. The fusion device as recited in claim 1, wherein the distal end is a drill bit.

13. A fusion device for fusion of a joint, comprising:
a distal end;
a proximal end;
a radially outward facing surface including threading;
a radially inward facing surface;
a bore extending from the proximal end;
at least one flute arranged proximate the distal end;
at least one aperture arranged adjacent to the at least one flute;
at least one opening; and,
at least one expandable member operatively arranged in the bore to expand radially through the at least one opening.

14. The fusion device as recited in claim 13, further comprising a plurality of fusion apertures extending from the radially outward facing surface to the bore.

15. The fusion device as recited in claim 13, wherein the proximal end further comprises a coupler operatively arranged to be non-rotatably connected to a hollow shaft.

16. The fusion device as recited in claim 13, further comprising a nut arranged in the bore, the nut operatively arranged to engage the at least one expandable member.

17. The fusion device as recited in claim 16, wherein when the nut is displaced in a first axial direction relative to the proximal end, the at least one expandable member displaces radially outward from the radially outward facing surface.

18. The fusion device as recited in claim 13, wherein the at least one expandable member comprises:
a first pivot fixedly secured to the radially inward facing surface;
a second pivot slidably connected to the radially inward facing surface; and,
a third pivot, wherein when the first pivot is displaced in a first axial direction relative to the proximal end, the third pivot displaces radially outward from the radially outward facing surface.

19. The fusion device assembly as recited in claim 13, wherein the at least one expandable member is pivotably connected to the radially inward facing surface.

20. A fusion device assembly for fusion of a joint, comprising:
a fusion device, including:
a distal end having a drill bit;
a proximal end;
a radially outward facing surface including threading;
a bore extending from the proximal end;
at least one flute arranged proximate the distal end;
at least one aperture arranged adjacent to the at least one flute;
at least one opening; and,
at least one expandable member operatively arranged in the bore to expand radially through the at least one opening; and,
a shaft, including:
a first end;
a second end operatively arranged to be non-rotatably connected to the proximal end; and,
a through-bore extending from the first end to the second end.

* * * * *